US012616472B2

(12) United States Patent (10) Patent No.: US 12,616,472 B2
Williams et al. (45) Date of Patent: *May 5, 2026

(54) ARTICULATING SURGICAL STAPLING APPARATUS WITH PIVOTABLE KNIFE BAR GUIDE ASSEMBLY

(71) Applicant: Covidien LP, Mansfield, MA (US)

(72) Inventors: Justin P. Williams, Southbury, CT (US); Griffin S. Delancy, Branford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/751,939

(22) Filed: Jun. 24, 2024

(65) Prior Publication Data

US 2024/0341763 A1 Oct. 17, 2024

Related U.S. Application Data

(63) Continuation of application No. 17/665,962, filed on Feb. 7, 2022, now Pat. No. 12,023,028, which is a (Continued)

(51) Int. Cl.
*A61B 17/072* (2006.01)
*A61B 17/29* (2006.01)

(52) U.S. Cl.
CPC .................... *A61B 17/07207* (2013.01); *A61B 2017/07271* (2013.01); *A61B 2017/07285* (2013.01); *A61B 2017/2927* (2013.01)

(58) Field of Classification Search
CPC .............. A61B 17/0686; A61B 17/072; A61B 17/07207; A61B 17/285; A61B 17/295;

(Continued)

(56) References Cited

U.S. PATENT DOCUMENTS 3,499,591 A 3/1970 Green
3,777,538 A 12/1973 Weatherly et al.
(Continued)

FOREIGN PATENT DOCUMENTS

AU 198654765 9/1986
CA 2773414 A1 11/2012
(Continued)

OTHER PUBLICATIONS

Extended European Search Report issued in corresponding European Application No. 23155384.3 dated Jun. 12, 2023, 13 pages.
(Continued)

*Primary Examiner* — Linda J. Hodge

(57) ABSTRACT

A surgical stapling apparatus includes a shaft assembly, an end effector secured to the shaft assembly, a firing assembly, an articulation assembly, and an articulation guide. The firing assembly includes a flexible knife bar assembly that is selectively advanceable through the end effector for firing the end effector. The articulation assembly has an articulation link assembly and a pivotable bar guide assembly. The articulation link assembly is coupled to the end effector. The articulation link assembly is actuatable to cause the end effector to move relative to the shaft assembly between an unarticulated position and an articulated position. The articulation guide is associated with the pivotable bar guide assembly to enable the flexible knife bar assembly to advance through the pivotable bar guide assembly when the end effector is disposed in the unarticulated position or the articulated position.

16 Claims, 16 Drawing Sheets

Related U.S. Application Data continuation-in-part of application No. 17/407,628, filed on Aug. 20, 2021, now Pat. No. 11,707,277.

(58) Field of Classification Search

CPC ...... A61B 17/2804; A61B 2017/07271; A61B 2017/07285; A61B 2017/07257; A61B 2017/07264; A61B 2017/07278; A61B 2017/2927; A61B 2017/00314; A61B 2017/00477; A61B 2017/2908; A61B 1/005; A61B 1/008

See application file for complete search history.

(56) References Cited

U.S. PATENT DOCUMENTS

| | | | |
|---|---|---|---|
| 3,882,854 A | 5/1975 | Hulka et al. | |
| 4,027,510 A | 6/1977 | Hiltebrandt | |
| 4,086,926 A | 5/1978 | Green et al. | |
| 4,241,861 A | 12/1980 | Fleischer | |
| 4,244,372 A | 1/1981 | Kapitanov et al. | |
| 4,429,695 A | 2/1984 | Green | |
| 4,505,414 A | 3/1985 | Filipi | |
| 4,520,817 A | 6/1985 | Green | |
| 4,589,413 A | 5/1986 | Malyshev et al. | |
| 4,596,351 A | 6/1986 | Fedotov et al. | |
| 4,602,634 A | 7/1986 | Barkley | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,633,861 A | 1/1987 | Chow et al. | |
| 4,633,874 A | 1/1987 | Chow et al. | |
| 4,671,445 A | 6/1987 | Barker et al. | |
| 4,700,703 A | 10/1987 | Resnick et al. | |
| 4,703,887 A | 11/1987 | Clanton et al. | |
| 4,728,020 A | 3/1988 | Green et al. | |
| 4,752,024 A | 6/1988 | Green et al. | |
| 4,784,137 A | 11/1988 | Kulik et al. | |
| 4,863,088 A | 9/1989 | Redmond et al. | |
| 4,869,415 A | 9/1989 | Fox | |
| 4,892,244 A | 1/1990 | Fox et al. | |
| 4,955,959 A | 9/1990 | Tompkins et al. | |
| 4,978,049 A | 12/1990 | Green | |
| 4,991,764 A | 2/1991 | Mericle | |
| 5,014,899 A | 5/1991 | Presty et al. | |
| 5,031,814 A | 7/1991 | Tompkins et al. | |
| 5,040,715 A | 8/1991 | Green et al. | |
| 5,065,929 A | 11/1991 | Schulze et al. | |
| 5,071,430 A | 12/1991 | de Salis et al. | |
| 5,074,454 A | 12/1991 | Peters | |
| 5,083,695 A | 1/1992 | Foslien et al. | |
| 5,084,057 A | 1/1992 | Green et al. | |
| 5,106,008 A | 4/1992 | Tompkins et al. | |
| 5,111,987 A | 5/1992 | Moeinzadeh et al. | |
| 5,129,570 A | 7/1992 | Schulze et al. | |
| 5,141,144 A | 8/1992 | Foslien et al. | |
| 5,156,315 A | 10/1992 | Green et al. | |
| 5,156,614 A | 10/1992 | Green et al. | |
| 5,163,943 A | 11/1992 | Mohiuddin et al. | |
| 5,170,925 A | 12/1992 | Madden et al. | |
| 5,171,247 A | 12/1992 | Hughett et al. | |
| 5,173,133 A | 12/1992 | Morin et al. | |
| 5,180,092 A | 1/1993 | Crainich | |
| 5,188,274 A | 2/1993 | Moeinzadeh et al. | |
| 5,220,928 A | 6/1993 | Oddsen et al. | |
| 5,221,036 A | 6/1993 | Takase | |
| 5,242,457 A | 9/1993 | Akopov et al. | |
| 5,246,156 A | 9/1993 | Rothfuss et al. | |
| 5,253,793 A | 10/1993 | Green et al. | |
| 5,263,629 A | 11/1993 | Trumbull et al. | |
| RE34,519 E | 1/1994 | Fox et al. | |
| 5,275,323 A | 1/1994 | Schulze et al. | |
| 5,289,963 A | 3/1994 | McGarry et al. | |
| 5,307,976 A | 5/1994 | Olson et al. | |
| 5,308,576 A | 5/1994 | Green et al. | |
| 5,312,023 A | 5/1994 | Green et al. | |
| 5,318,221 A | 6/1994 | Green et al. | |
| 5,326,013 A | 7/1994 | Green et al. | |
| 5,328,077 A | 7/1994 | Lou | |
| 5,330,486 A | 7/1994 | Wilk | |
| 5,332,142 A | 7/1994 | Robinson et al. | |
| 5,336,232 A | 8/1994 | Green et al. | |
| 5,344,061 A | 9/1994 | Crainich | |
| 5,352,238 A | 10/1994 | Green et al. | |
| 5,356,064 A * | 10/1994 | Green | A61B 17/0684 |
| | | | 606/139 |
| 5,358,506 A | 10/1994 | Green et al. | |
| 5,364,001 A | 11/1994 | Bryan | |
| 5,364,002 A | 11/1994 | Green et al. | |
| 5,364,003 A | 11/1994 | Williamson, IV | |
| 5,366,133 A | 11/1994 | Geiste | |
| 5,376,095 A | 12/1994 | Ortiz | |
| 5,379,933 A | 1/1995 | Green et al. | |
| 5,381,943 A | 1/1995 | Allen et al. | |
| 5,382,255 A | 1/1995 | Castro et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,395,034 A | 3/1995 | Allen et al. | |
| 5,397,046 A | 3/1995 | Savage et al. | |
| 5,397,324 A | 3/1995 | Carroll et al. | |
| 5,403,312 A | 4/1995 | Yates et al. | |
| 5,405,072 A | 4/1995 | Zlock et al. | |
| 5,407,293 A | 4/1995 | Crainich | |
| 5,413,268 A | 5/1995 | Green et al. | |
| 5,415,334 A | 5/1995 | Williamson et al. | |
| 5,415,335 A | 5/1995 | Knodell, Jr. | |
| 5,417,361 A | 5/1995 | Williamson, IV | |
| 5,423,471 A * | 6/1995 | Mastri | A61B 17/068 |
| | | | 227/181.1 |
| 5,425,745 A | 6/1995 | Green et al. | |
| 5,431,322 A | 7/1995 | Green et al. | |
| 5,431,323 A | 7/1995 | Smith et al. | |
| 5,433,721 A | 7/1995 | Hooven et al. | |
| 5,441,193 A | 8/1995 | Gravener | |
| 5,445,304 A | 8/1995 | Plyley et al. | |
| 5,447,265 A | 9/1995 | Vidal et al. | |
| 5,452,837 A | 9/1995 | Williamson, IV et al. | |
| 5,456,401 A | 10/1995 | Green et al. | |
| 5,464,300 A | 11/1995 | Crainich | |
| 5,465,895 A | 11/1995 | Knodel et al. | |
| 5,467,911 A | 11/1995 | Tsuruta et al. | |
| 5,470,007 A | 11/1995 | Plyley et al. | |
| 5,470,010 A | 11/1995 | Rothfuss et al. | |
| 5,472,132 A | 12/1995 | Savage et al. | |
| 5,474,566 A | 12/1995 | Alesi et al. | |
| 5,476,206 A | 12/1995 | Green et al. | |
| 5,478,003 A | 12/1995 | Green et al. | |
| 5,480,089 A | 1/1996 | Blewett | |
| 5,482,197 A | 1/1996 | Green et al. | |
| 5,484,095 A | 1/1996 | Green et al. | |
| 5,484,451 A | 1/1996 | Akopov et al. | |
| 5,485,947 A | 1/1996 | Olson et al. | |
| 5,485,952 A | 1/1996 | Fontayne | |
| 5,486,185 A | 1/1996 | Freitas et al. | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,490,856 A | 2/1996 | Person et al. | |
| 5,497,933 A | 3/1996 | DeFonzo et al. | |
| 5,501,689 A | 3/1996 | Green et al. | |
| 5,505,363 A | 4/1996 | Green et al. | |
| 5,507,426 A | 4/1996 | Young et al. | |
| 5,518,163 A | 5/1996 | Hooven | |
| 5,518,164 A | 5/1996 | Hooven | |
| 5,529,235 A | 6/1996 | Boiarski et al. | |
| 5,531,744 A | 7/1996 | Nardella et al. | |
| 5,535,934 A | 7/1996 | Boiarski et al. | |
| 5,535,935 A | 7/1996 | Vidal et al. | |
| 5,535,937 A | 7/1996 | Boiarski et al. | |
| 5,540,375 A | 7/1996 | Bolanos et al. | |
| 5,542,594 A | 8/1996 | McKean et al. | |
| 5,549,628 A | 8/1996 | Cooper et al. | |
| 5,551,622 A | 9/1996 | Yoon | |
| 5,553,765 A | 9/1996 | Knodel et al. | |

(56)                References Cited

U.S. PATENT DOCUMENTS

| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,690,675 A | 11/1997 | Sawyer et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,394 A | 10/1999 | Robertson |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |

(56)        References Cited

U.S. PATENT DOCUMENTS

| | | | |
|---|---|---|---|
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |

(56)     References Cited

U.S. PATENT DOCUMENTS

| | | | |
|---|---|---|---|
| 7,513,408 B2 | 4/2009 | Shelton, IV et al. |
| 7,517,356 B2 | 4/2009 | Heinrich |
| 7,537,602 B2 | 5/2009 | Whilman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |

(56) References Cited

U.S. PATENT DOCUMENTS

| | | |
|---|---|---|
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,405 B2 | 2/2012 | Milliman |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |

(56) References Cited

U.S. PATENT DOCUMENTS

| | | | |
|---|---|---|---|
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Whitman et al. |
| 8,544,111 B2 | 9/2013 | Shintani et al. |
| 8,550,325 B2 | 10/2013 | Cohen et al. |

(56)  References Cited

U.S. PATENT DOCUMENTS

| | | | |
|---|---|---|---|
| 8,556,151 | B2 | 10/2013 | Viola |
| 8,561,870 | B2 | 10/2013 | Baxter, III et al. |
| 8,561,873 | B2 | 10/2013 | Ingmanson et al. |
| 8,561,874 | B2 | 10/2013 | Scirica |
| 8,567,656 | B2 | 10/2013 | Shelton, IV et al. |
| 8,573,461 | B2 | 11/2013 | Shelton, IV et al. |
| 8,573,463 | B2 | 11/2013 | Scirica et al. |
| 8,573,465 | B2 | 11/2013 | Shelton, IV |
| 8,579,176 | B2 | 11/2013 | Smith et al. |
| 8,579,177 | B2 | 11/2013 | Beetel |
| 8,584,919 | B2 | 11/2013 | Hueil et al. |
| 8,584,920 | B2 | 11/2013 | Hodgkinson |
| 8,590,762 | B2 | 11/2013 | Hess et al. |
| 8,596,515 | B2 | 12/2013 | Okoniewski |
| 8,597,311 | B2 | 12/2013 | Criscuolo et al. |
| 8,602,288 | B2 | 12/2013 | Shelton, IV et al. |
| 8,608,045 | B2 | 12/2013 | Smith et al. |
| 8,608,046 | B2 | 12/2013 | Laurent et al. |
| 8,608,047 | B2 | 12/2013 | Holsten et al. |
| 8,613,383 | B2 | 12/2013 | Beckman et al. |
| 8,613,384 | B2 | 12/2013 | Pastorelli et al. |
| 8,616,427 | B2 | 12/2013 | Viola |
| 8,616,430 | B2 | 12/2013 | (Prommersberger) Stopek et al. |
| 8,627,994 | B2 | 1/2014 | Zemlok et al. |
| 8,628,544 | B2 | 1/2014 | Farascioni |
| 8,631,988 | B2 | 1/2014 | Viola |
| 8,631,989 | B2 | 1/2014 | Aranyi et al. |
| 8,631,991 | B2 | 1/2014 | Cropper et al. |
| 8,632,525 | B2 | 1/2014 | Kerr et al. |
| 8,632,535 | B2 | 1/2014 | Shelton, IV et al. |
| 8,636,187 | B2 | 1/2014 | Hueil et al. |
| 8,636,190 | B2 | 1/2014 | Zemlok et al. |
| 8,636,192 | B2 | 1/2014 | Farascioni et al. |
| 8,636,762 | B2 | 1/2014 | Whitman et al. |
| 8,636,766 | B2 | 1/2014 | Milliman et al. |
| 8,640,940 | B2 | 2/2014 | Ohdaira |
| 8,657,174 | B2 | 2/2014 | Yates et al. |
| 8,657,177 | B2 | 2/2014 | Scirica et al. |
| 8,657,178 | B2 | 2/2014 | Hueil et al. |
| 8,662,371 | B2 | 3/2014 | Viola |
| 8,668,129 | B2 | 3/2014 | Olson |
| 8,672,206 | B2 | 3/2014 | Aranyi et al. |
| 8,672,208 | B2 | 3/2014 | Hess et al. |
| 8,672,209 | B2 | 3/2014 | Crainich |
| 8,678,263 | B2 | 3/2014 | Viola |
| 8,678,990 | B2 | 3/2014 | Wazer et al. |
| 8,679,155 | B2 | 3/2014 | Knodel et al. |
| 8,684,247 | B2 | 4/2014 | Scirica et al. |
| 8,684,249 | B2 | 4/2014 | Racenet et al. |
| 8,684,253 | B2 | 4/2014 | Giordano et al. |
| 8,690,039 | B2 | 4/2014 | Beardsley et al. |
| 8,695,865 | B2 | 4/2014 | Smith et al. |
| 8,695,866 | B2 | 4/2014 | Leimbach et al. |
| 8,701,958 | B2 | 4/2014 | Shelton, IV et al. |
| 8,701,959 | B2 | 4/2014 | Shah |
| 8,701,961 | B2 | 4/2014 | Ivanko |
| 8,708,213 | B2 | 4/2014 | Shelton, IV et al. |
| 8,714,429 | B2 | 5/2014 | Demmy |
| 8,715,277 | B2 | 5/2014 | Weizman |
| 8,720,766 | B2 | 5/2014 | Hess et al. |
| 8,721,630 | B2 | 5/2014 | Ortiz et al. |
| 8,727,197 | B2 | 5/2014 | Hess et al. |
| 8,727,200 | B2 | 5/2014 | Roy |
| 8,733,612 | B2 | 5/2014 | Ma |
| 8,740,034 | B2 | 6/2014 | Morgan et al. |
| 8,740,039 | B2 | 6/2014 | Farascioni |
| 8,746,529 | B2 | 6/2014 | Shelton, IV et al. |
| 8,746,530 | B2 | 6/2014 | Giordano et al. |
| 8,746,533 | B2 | 6/2014 | Whitman |
| 8,746,534 | B2 | 6/2014 | Farascioni |
| 8,746,535 | B2 | 6/2014 | Shelton, IV et al. |
| 8,747,421 | B2 | 6/2014 | Balbierz et al. |
| 8,752,747 | B2 | 6/2014 | Shelton, IV et al. |
| 8,752,748 | B2 | 6/2014 | Whitman et al. |
| 8,752,749 | B2 | 6/2014 | Moore et al. |
| 8,757,465 | B2 | 6/2014 | Woodard, Jr. et al. |
| 8,758,391 | B2 | 6/2014 | Swayze et al. |
| 8,763,875 | B2 | 7/2014 | Morgan et al. |
| 8,763,876 | B2 | 7/2014 | Kostrzewski |
| 8,763,877 | B2 | 7/2014 | Schall et al. |
| 8,763,879 | B2 | 7/2014 | Shelton, IV et al. |
| 8,770,458 | B2 | 7/2014 | Scirica |
| 8,777,082 | B2 | 7/2014 | Scirica |
| 8,783,541 | B2 | 7/2014 | Shelton, IV et al. |
| 8,783,542 | B2 | 7/2014 | Riestenberg et al. |
| 8,789,737 | B2 | 7/2014 | Hodgkinson et al. |
| 8,789,738 | B2 | 7/2014 | Knodel et al. |
| 8,789,739 | B2 | 7/2014 | Swensgard |
| 8,800,838 | B2 | 8/2014 | Shelton, IV |
| 8,800,840 | B2 | 8/2014 | Jankowski |
| 8,800,841 | B2 | 8/2014 | Ellerhorst et al. |
| 8,806,973 | B2 | 8/2014 | Ross et al. |
| 8,808,311 | B2 | 8/2014 | Heinrich et al. |
| 8,814,024 | B2 | 8/2014 | Woodard, Jr. et al. |
| 8,814,025 | B2 | 8/2014 | Miller et al. |
| 8,820,603 | B2 | 9/2014 | Shelton, IV et al. |
| 8,820,605 | B2 | 9/2014 | Shelton, IV |
| 8,820,606 | B2 | 9/2014 | Hodgkinson |
| 8,820,607 | B2 | 9/2014 | Marczyk |
| 8,827,133 | B2 | 9/2014 | Shelton, IV et al. |
| 8,827,134 | B2 | 9/2014 | Viola et al. |
| 8,833,631 | B2 | 9/2014 | Munro, III et al. |
| 8,833,632 | B2 | 9/2014 | Swensgard |
| 8,840,003 | B2 | 9/2014 | Morgan et al. |
| 8,840,603 | B2 | 9/2014 | Shelton, IV et al. |
| 8,844,788 | B2 | 9/2014 | Knodel |
| 8,851,354 | B2 | 10/2014 | Swensgard et al. |
| 8,851,355 | B2 | 10/2014 | Aranyi et al. |
| 8,857,693 | B2 | 10/2014 | Schuckmann et al. |
| 8,864,007 | B2 | 10/2014 | Widenhouse et al. |
| 8,864,009 | B2 | 10/2014 | Shelton, IV et al. |
| 8,864,010 | B2 | 10/2014 | Williams |
| 8,870,050 | B2 | 10/2014 | Hodgkinson |
| 8,875,971 | B2 | 11/2014 | Hall et al. |
| 8,875,972 | B2 | 11/2014 | Weisenburgh, II et al. |
| 8,893,949 | B2 | 11/2014 | Shelton, IV et al. |
| 8,893,950 | B2 | 11/2014 | Marczyk |
| 8,899,461 | B2 | 12/2014 | Farascioni |
| 8,899,462 | B2 | 12/2014 | Kostrzewski et al. |
| 8,899,463 | B2 | 12/2014 | Schall et al. |
| 8,899,464 | B2 | 12/2014 | Hueil et al. |
| 8,900,616 | B2 | 12/2014 | Belcheva et al. |
| 8,920,435 | B2 | 12/2014 | Smith et al. |
| 8,925,782 | B2 | 1/2015 | Shelton, IV |
| 8,926,598 | B2 | 1/2015 | Mollere et al. |
| 8,931,681 | B2 | 1/2015 | Kostrzewski |
| 8,931,682 | B2 | 1/2015 | Timm et al. |
| 8,931,693 | B1 | 1/2015 | Kumar et al. |
| 8,955,732 | B2 | 2/2015 | Zemlok et al. |
| 8,958,429 | B2 | 2/2015 | Shukla et al. |
| 8,960,517 | B2 | 2/2015 | Lee |
| 8,960,520 | B2 | 2/2015 | McCuen |
| 8,967,443 | B2 | 3/2015 | McCuen |
| 8,967,446 | B2 | 3/2015 | Beardsley et al. |
| 8,973,803 | B2 | 3/2015 | Hall et al. |
| 8,978,954 | B2 | 3/2015 | Shelton, IV et al. |
| 8,978,956 | B2 | 3/2015 | Schall et al. |
| 8,991,677 | B2 | 3/2015 | Moore et al. |
| 8,991,678 | B2 | 3/2015 | Wellman et al. |
| 8,998,058 | B2 | 4/2015 | Moore et al. |
| 8,998,060 | B2 | 4/2015 | Bruewer et al. |
| 9,005,230 | B2 | 4/2015 | Yates et al. |
| 9,010,606 | B2 | 4/2015 | Aranyi et al. |
| 9,010,607 | B2 | 4/2015 | Kostrzewski |
| 9,010,610 | B2 | 4/2015 | Hodgkinson |
| 9,016,539 | B2 | 4/2015 | Kostrzewski et al. |
| 9,016,541 | B2 | 4/2015 | Viola et al. |
| 9,016,542 | B2 | 4/2015 | Shelton, IV et al. |
| 9,016,544 | B2 | 4/2015 | Hodgkinson et al. |
| 9,016,545 | B2 | 4/2015 | Aranyi et al. |
| 9,016,546 | B2 | 4/2015 | Demmy et al. |
| 9,017,371 | B2 | 4/2015 | Whitman et al. |
| 9,022,271 | B2 | 5/2015 | Scirica |
| 9,027,817 | B2 | 5/2015 | Milliman et al. |

(56) References Cited

U.S. PATENT DOCUMENTS

| | | | |
|---|---|---|---|
| 9,033,203 B2 | 5/2015 | Woodard, Jr. et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,084,601 B2 | 7/2015 | Moore et al. |
| 9,084,602 B2 | 7/2015 | Gleiman |
| 9,089,326 B2 | 7/2015 | Krumanaker et al. |
| 9,095,339 B2 | 8/2015 | Moore et al. |
| 9,101,359 B2 | 8/2015 | Smith et al. |
| 9,107,663 B2 | 8/2015 | Swensgard |
| 9,107,664 B2 | 8/2015 | Marczyk |
| 9,107,667 B2 | 8/2015 | Hodgkinson |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,660 B2 | 12/2015 | Hodgkinson |
| 9,198,661 B2 | 12/2015 | Swensgard |
| 9,198,662 B2 | 12/2015 | Barton et al. |
| 9,204,876 B2 | 12/2015 | Cappola et al. |
| 9,204,877 B2 | 12/2015 | Whitman et al. |
| 9,204,880 B2 | 12/2015 | Baxter, III et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,237,892 B2 | 1/2016 | Hodgkinson |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,771 B2 | 5/2016 | Baxter, III et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,479 B2 | 5/2016 | (Tarinelli) Racenet et al. |
| 9,345,481 B2 | 5/2016 | Hall et al. |
| 9,345,780 B2 | 5/2016 | Manoharan et al. |
| 9,351,726 B2 | 5/2016 | Leimbach |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,227 B2 | 6/2016 | Kostrzewski |
| 9,364,231 B2 | 6/2016 | Wenchell |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,402,627 B2 | 8/2016 | Stevenson et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,498,219 B2 | 11/2016 | Moore et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,522,002 B2 | 12/2016 | Chowaniec et al. |
| 9,539,007 B2 | 1/2017 | Dhakad et al. |
| 9,549,735 B2 | 1/2017 | Shelton, IV et al. |
| 9,554,794 B2 | 1/2017 | Baber |
| 9,561,029 B2 | 2/2017 | Scheib et al. |
| 9,561,031 B2 | 2/2017 | Heinrich et al. |
| 9,566,065 B2 | 2/2017 | Knodel |
| 9,572,576 B2 | 2/2017 | Hodgkinson et al. |
| 9,579,101 B2 | 2/2017 | Whitman et al. |
| 9,585,657 B2 | 3/2017 | Shelton, IV et al. |
| 9,585,662 B2 | 3/2017 | Shelton, IV et al. |
| 9,597,077 B2 | 3/2017 | Hodgkinson |
| 9,610,080 B2 | 4/2017 | Whitfield et al. |
| 9,615,825 B2 | 4/2017 | Viola |
| 9,615,826 B2 | 4/2017 | Shelton, IV et al. |
| 9,622,746 B2 | 4/2017 | Simms |
| 9,629,623 B2 | 4/2017 | Lytle, IV et al. |
| 9,629,626 B2 | 4/2017 | Soltz et al. |
| 9,629,628 B2 | 4/2017 | Aranyi |
| 9,629,629 B2 | 4/2017 | Leimbach et al. |
| 9,642,620 B2 | 5/2017 | Baxter, III |
| 9,649,109 B2 | 5/2017 | Ranucci et al. |
| 9,655,613 B2 | 5/2017 | Schaller |
| 9,662,108 B2 | 5/2017 | Williams |
| 9,668,728 B2 | 6/2017 | Williams et al. |
| 9,668,732 B2 | 6/2017 | Patel et al. |
| 9,675,351 B2 | 6/2017 | Hodgkinson et al. |
| 9,681,870 B2 | 6/2017 | Baxter, III et al. |
| 9,687,230 B2 | 6/2017 | Leimbach et al. |
| 9,687,233 B2 | 6/2017 | Fernandez et al. |
| 9,693,772 B2 | 7/2017 | Ingmanson et al. |
| 9,700,309 B2 | 7/2017 | Jaworek |
| 9,700,319 B2 | 7/2017 | Motooka et al. |
| 9,706,993 B2 | 7/2017 | Hessler et al. |
| 9,713,470 B2 | 7/2017 | Scirica et al. |
| 9,713,474 B2 | 7/2017 | Lorenz |
| 9,717,497 B2 | 8/2017 | Zerkle et al. |
| 9,717,498 B2 | 8/2017 | Aranyi et al. |
| 9,724,092 B2 | 8/2017 | Baxter, III et al. |
| 9,724,095 B2 | 8/2017 | Gupta et al. |
| 9,763,662 B2 | 9/2017 | Shelton, IV et al. |
| 9,770,245 B2 | 9/2017 | Swayze et al. |
| 9,775,610 B2 | 10/2017 | Nicholas et al. |

(56) References Cited

U.S. PATENT DOCUMENTS

| | | | |
|---|---|---|---|
| 9,775,635 B2 | 10/2017 | Takei |
| 9,782,169 B2 | 10/2017 | Kimsey |
| 9,782,173 B2 | 10/2017 | Mozdzierz |
| 9,795,379 B2 | 10/2017 | Leimbach et al. |
| 9,795,384 B2 | 10/2017 | Weaner et al. |
| 9,808,246 B2 | 11/2017 | Shelton, IV |
| 9,808,248 B2 | 11/2017 | Hoffman |
| 9,808,249 B2 | 11/2017 | Shelton, IV |
| 9,820,741 B2 | 11/2017 | Kostrzewski |
| 9,820,742 B2 | 11/2017 | Covach et al. |
| 9,827,002 B2 | 11/2017 | Hausen et al. |
| 9,839,420 B2 | 12/2017 | Shelton, IV |
| 9,839,421 B2 | 12/2017 | Zerkle et al. |
| 9,839,428 B2 | 12/2017 | Baxter, III et al. |
| 9,855,038 B2 | 1/2018 | Smith et al. |
| 9,855,040 B2 | 1/2018 | Kostrzewski |
| 9,861,358 B2 | 1/2018 | Marczyk et al. |
| 9,861,359 B2 | 1/2018 | Shelton, IV et al. |
| 9,867,612 B2 | 1/2018 | Parihar et al. |
| 9,867,613 B2 | 1/2018 | Marczyk et al. |
| 9,867,615 B2 | 1/2018 | Fanelli et al. |
| 9,872,683 B2 | 1/2018 | Hopkins |
| 9,883,860 B2 | 2/2018 | Leimbach et al. |
| 9,901,342 B2 | 2/2018 | Shelton, IV et al. |
| 9,913,646 B2 | 3/2018 | Shelton, IV |
| 9,918,714 B2 | 3/2018 | Gibbons, Jr. |
| 9,918,717 B2 | 3/2018 | Czemik |
| 9,924,941 B2 | 3/2018 | Burbank |
| 9,924,942 B2 | 3/2018 | Swayze et al. |
| 9,936,951 B2 | 4/2018 | Hufnagel et al. |
| 9,936,954 B2 | 4/2018 | Shelton, IV et al. |
| 9,943,311 B2 | 4/2018 | Scirica et al. |
| 9,949,737 B2 | 4/2018 | Zergiebel et al. |
| 9,955,966 B2 | 5/2018 | Zergiebel |
| 9,968,354 B2 | 5/2018 | Shelton, IV et al. |
| 9,980,724 B2 | 5/2018 | Farascioni et al. |
| 9,987,012 B2 | 6/2018 | Shah |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 10,004,497 B2 | 6/2018 | Overmyer et al. |
| 10,004,505 B2 | 6/2018 | Moore et al. |
| 10,034,668 B2 | 7/2018 | Ebner |
| 10,039,532 B2 | 8/2018 | Srinivas et al. |
| 10,039,545 B2 | 8/2018 | Sadowski et al. |
| 10,045,782 B2 | 8/2018 | Murthy Aravalli |
| 10,052,044 B2 | 8/2018 | Shelton, IV et al. |
| 10,058,963 B2 | 8/2018 | Shelton, IV et al. |
| 10,064,622 B2 | 9/2018 | Murthy Aravalli |
| 10,076,325 B2 | 9/2018 | Huang et al. |
| 10,085,750 B2 | 10/2018 | Zergiebel et al. |
| 10,092,290 B2 | 10/2018 | Yigit et al. |
| 10,092,292 B2 | 10/2018 | Boudreaux et al. |
| 10,111,657 B2 | 10/2018 | McCuen |
| 10,111,665 B2 | 10/2018 | Aranyi |
| 10,117,650 B2 | 11/2018 | Nicholas et al. |
| 10,117,654 B2 | 11/2018 | Ingmanson et al. |
| 10,123,796 B2 | 11/2018 | Westling et al. |
| 10,123,798 B2 | 11/2018 | Baxter, III et al. |
| 10,135,242 B2 | 11/2018 | Baber et al. |
| 10,143,474 B2 | 12/2018 | Bucciaglia et al. |
| 10,172,612 B2 | 1/2019 | Frushour |
| 10,172,615 B2 | 1/2019 | Marczyk et al. |
| 10,172,617 B2 | 1/2019 | Shelton, IV et al. |
| 10,175,127 B2 | 1/2019 | Collins et al. |
| 10,180,463 B2 | 1/2019 | Beckman et al. |
| 10,182,816 B2 | 1/2019 | Shelton, IV et al. |
| 10,206,677 B2 | 2/2019 | Harris et al. |
| 10,213,201 B2 | 2/2019 | Shelton, IV et al. |
| 10,219,804 B2 | 3/2019 | Linder et al. |
| 10,226,239 B2 | 3/2019 | Nicholas et al. |
| 10,226,250 B2 | 3/2019 | Beckman et al. |
| 10,226,254 B2 | 3/2019 | Cabrera et al. |
| 10,245,033 B2 | 4/2019 | Overmyer et al. |
| 10,245,038 B2 | 4/2019 | Hopkins et al. |
| 10,251,725 B2 | 4/2019 | Valentine et al. |
| 10,265,065 B2 | 4/2019 | Shelton, IV et al. |
| 10,265,066 B2 | 4/2019 | Measamer et al. |
| 10,265,074 B2 | 4/2019 | Shelton, IV et al. |
| 10,271,840 B2 | 4/2019 | Sapre |
| 10,271,841 B2 | 4/2019 | Overmyer et al. |
| 10,285,694 B2 | 5/2019 | Viola et al. |
| 10,285,698 B2 | 5/2019 | Cappola et al. |
| 10,321,907 B2 | 6/2019 | Shelton, IV et al. |
| 10,327,776 B2 | 6/2019 | Harris et al. |
| 10,335,150 B2 | 7/2019 | Shelton, IV |
| 10,349,939 B2 | 7/2019 | Shelton, IV et al. |
| 10,349,941 B2 | 7/2019 | Marczyk et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,405,857 B2 | 9/2019 | Shelton |
| 10,426,468 B2 | 10/2019 | Contini et al. |
| 10,441,279 B2 | 10/2019 | Shelton, IV et al. |
| 10,456,129 B2 | 10/2019 | Shelton, IV et al. |
| 10,456,130 B2 | 10/2019 | Cheney et al. |
| 10,463,368 B2 | 11/2019 | Kostrzewski |
| 10,470,762 B2 | 11/2019 | Leimbach et al. |
| 10,470,911 B2 | 11/2019 | Thompson et al. |
| 10,478,182 B2 | 11/2019 | Taylor |
| 10,478,183 B2 | 11/2019 | Hess et al. |
| 10,478,187 B2 | 11/2019 | Shelton, IV et al. |
| 10,542,976 B2 | 1/2020 | Calderoni et al. |
| 10,548,504 B2 | 2/2020 | Shelton, IV et al. |
| 10,548,593 B2 | 2/2020 | Shelton, IV et al. |
| 10,548,599 B2 | 2/2020 | Marczyk et al. |
| 10,561,417 B2 | 2/2020 | Zergiebel et al. |
| 10,561,418 B2 | 2/2020 | Richard et al. |
| 10,568,621 B2 | 2/2020 | Shelton, IV et al. |
| 10,588,629 B2 | 3/2020 | Malinouskas et al. |
| 10,595,929 B2 | 3/2020 | Boudreaux et al. |
| 10,603,128 B2 | 3/2020 | Zergiebel et al. |
| 10,617,412 B2 | 4/2020 | Shelton, IV et al. |
| 10,624,634 B2 | 4/2020 | Shelton, IV et al. |
| 10,687,806 B2 | 6/2020 | Shelton, IV et al. |
| 10,695,053 B2 | 6/2020 | Hess et al. |
| 10,779,822 B2 | 9/2020 | Yates et al. |
| 10,792,038 B2 | 10/2020 | Becerra et al. |
| 10,828,030 B2 | 11/2020 | Weir et al. |
| 10,863,984 B2 | 12/2020 | Shelton, IV et al. |
| 12,023,028 B2 * | 7/2024 | Williams ......... A61B 17/07207 |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |

(56) References Cited

U.S. PATENT DOCUMENTS

| | | |
|---|---|---|
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0308907 A1 | 12/2009 | Nalagatla et al. |
| 2010/0012703 A1 | 1/2010 | Calabrese et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0087276 A1 | 4/2011 | Bedi et al. |
| 2011/0101069 A1 | 5/2011 | Bombard et al. |
| 2011/0147433 A1 | 6/2011 | Shelton, IV et al. |
| 2011/0163146 A1 | 7/2011 | Ortiz et al. |
| 2011/0192882 A1 | 8/2011 | Hess et al. |
| 2011/0278343 A1 | 11/2011 | Knodel et al. |
| 2011/0290856 A1 | 12/2011 | Shelton, IV et al. |
| 2012/0053406 A1 | 3/2012 | Conlon et al. |
| 2012/0061446 A1 | 3/2012 | Knodel et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0116416 A1 | 5/2012 | Neff et al. |
| 2012/0138659 A1 | 6/2012 | Marczyk et al. |
| 2012/0193394 A1 | 8/2012 | Holcomb et al. |
| 2012/0193399 A1 | 8/2012 | Holcomb et al. |
| 2012/0211542 A1 | 8/2012 | Racenet |
| 2012/0228358 A1 | 9/2012 | Zemlok et al. |
| 2012/0234895 A1 | 9/2012 | O'Connor et al. |
| 2012/0234897 A1 | 9/2012 | Shelton, IV et al. |
| 2012/0241504 A1 | 9/2012 | Soltz et al. |
| 2012/0248169 A1 | 10/2012 | Widenhouse et al. |
| 2012/0286022 A1 | 11/2012 | Oson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0041406 A1 | 2/2013 | Bear et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0098970 A1 | 4/2013 | Racenet et al. |
| 2013/0153641 A1 | 6/2013 | Shelton, IV et al. |
| 2013/0175316 A1 | 7/2013 | Thompson et al. |
| 2013/0256380 A1 | 10/2013 | Schmid et al. |
| 2013/0277410 A1 | 10/2013 | Fernandez et al. |
| 2013/0334280 A1 | 12/2013 | Krehel et al. |
| 2014/0014704 A1 | 1/2014 | Onukuri et al. |
| 2014/0014707 A1 | 1/2014 | Onukuri et al. |
| 2014/0048580 A1 | 2/2014 | Merchant et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175150 A1 | 6/2014 | Shelton, IV et al. |
| 2014/0239047 A1 | 8/2014 | Hodgkinson et al. |
| 2014/0246475 A1 | 9/2014 | Hall et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0263558 A1 | 9/2014 | Hausen et al. |
| 2014/0284371 A1 | 9/2014 | Morgan et al. |
| 2014/0291379 A1 | 10/2014 | Schellin et al. |
| 2014/0291383 A1 | 10/2014 | Spivey et al. |
| 2014/0367445 A1 | 12/2014 | Ingmanson et al. |
| 2015/0076211 A1 | 3/2015 | Irka et al. |
| 2015/0134076 A1 | 5/2015 | Shelton, IV et al. |
| 2015/0173749 A1 | 6/2015 | Shelton, IV et al. |
| 2015/0173756 A1 | 6/2015 | Baxter, III et al. |
| 2015/0250474 A1 | 9/2015 | Abbott et al. |
| 2015/0272557 A1 | 10/2015 | Overmyer et al. |
| 2015/0297222 A1 | 10/2015 | Huitema et al. |
| 2015/0297225 A1 | 10/2015 | Huitema et al. |
| 2015/0374372 A1 | 12/2015 | Zergiebel et al. |
| 2016/0066909 A1 | 3/2016 | Baber et al. |
| 2016/0166249 A1 | 6/2016 | Knodel |
| 2016/0166253 A1 | 6/2016 | Knodel |
| 2016/0174972 A1* | 6/2016 | Shelton, IV ......... A61B 17/072 227/180.1 |
| 2016/0235494 A1 | 8/2016 | Shelton, IV et al. |
| 2016/0302791 A1 | 10/2016 | Schmitt |
| 2016/0354176 A1 | 12/2016 | Schmitt |
| 2017/0000483 A1 | 1/2017 | Motai et al. |
| 2017/0224336 A1 | 8/2017 | Hunter et al. |
| 2017/0224343 A1* | 8/2017 | Baxter, III ........... A61B 17/072 |
| 2018/0168603 A1 | 6/2018 | Morgan et al. |
| 2018/0317913 A1 | 11/2018 | Beardsley |
| 2018/0368839 A1 | 12/2018 | Shelton, IV |
| 2019/0288089 A9* | 9/2019 | Fareed ................. H10D 30/015 |
| 2020/0315622 A1* | 10/2020 | Kostrzewski ........ A61B 17/072 |

FOREIGN PATENT DOCUMENTS

| | | | |
|---|---|---|---|
| CA | 2884962 A1 | 11/2015 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |

(56)          References Cited

FOREIGN PATENT DOCUMENTS

| | | | | |
|---|---|---|---|---|
| EP | 0656188 | A2 | 6/1995 | |
| EP | 0666057 | A2 | 8/1995 | |
| EP | 0705571 | A1 | 4/1996 | |
| EP | 0760230 | A1 | 3/1997 | |
| EP | 1952769 | A2 | 8/2008 | |
| EP | 2090253 | A2 | 8/2009 | |
| EP | 2090254 | A1 | 8/2009 | |
| EP | 2583630 | A2 | 4/2013 | |
| EP | 2586382 | A2 | 5/2013 | |
| EP | 2907456 | A1 | 8/2015 | |
| EP | 3398528 | A1 * | 11/2018 | ....... A61B 17/00234 |
| EP | 3636167 | A1 | 4/2020 | |
| EP | 3718484 | A1 | 10/2020 | |
| EP | 3970629 | A1 | 3/2022 | |
| FR | 391239 | A | 10/1908 | |
| FR | 2542188 | A1 | 9/1984 | |
| FR | 2660851 | A1 | 10/1991 | |
| FR | 2681775 | A1 | 4/1993 | |
| GB | 1352554 | A | 5/1974 | |
| GB | 1452185 | A | 10/1976 | |
| GB | 1555455 | A | 11/1979 | |
| GB | 2048685 | A | 12/1980 | |
| GB | 2070499 | A | 9/1981 | |
| GB | 2141066 | A | 12/1984 | |
| GB | 2165559 | A | 4/1986 | |
| JP | 51149985 | | 12/1976 | |
| JP | 2001087272 | | 4/2001 | |
| SU | 659146 | A1 | 4/1979 | |
| SU | 728848 | A1 | 4/1980 | |
| SU | 980703 | A1 | 12/1982 | |
| SU | 990220 | A1 | 1/1983 | |
| WO | 2008302247 | | 7/1983 | |
| WO | 8910094 | A1 | 11/1989 | |
| WO | 9210976 | A1 | 7/1992 | |
| WO | 9308754 | A1 | 5/1993 | |
| WO | 9314706 | A1 | 8/1993 | |
| WO | 2004032760 | A2 | 4/2004 | |
| WO | 2009071070 | A2 | 6/2009 | |
| WO | 20150191887 | A1 | 12/2015 | |
| WO | 2016025132 | A1 | 2/2016 | |
| WO | 2016099959 | A2 | 6/2016 | |
| WO | 2017139155 | A1 | 8/2017 | |

OTHER PUBLICATIONS

International Search Report and Written Opinion for application No. PCT/IB2022/057650 dated Nov. 23, 2022.

* cited by examiner

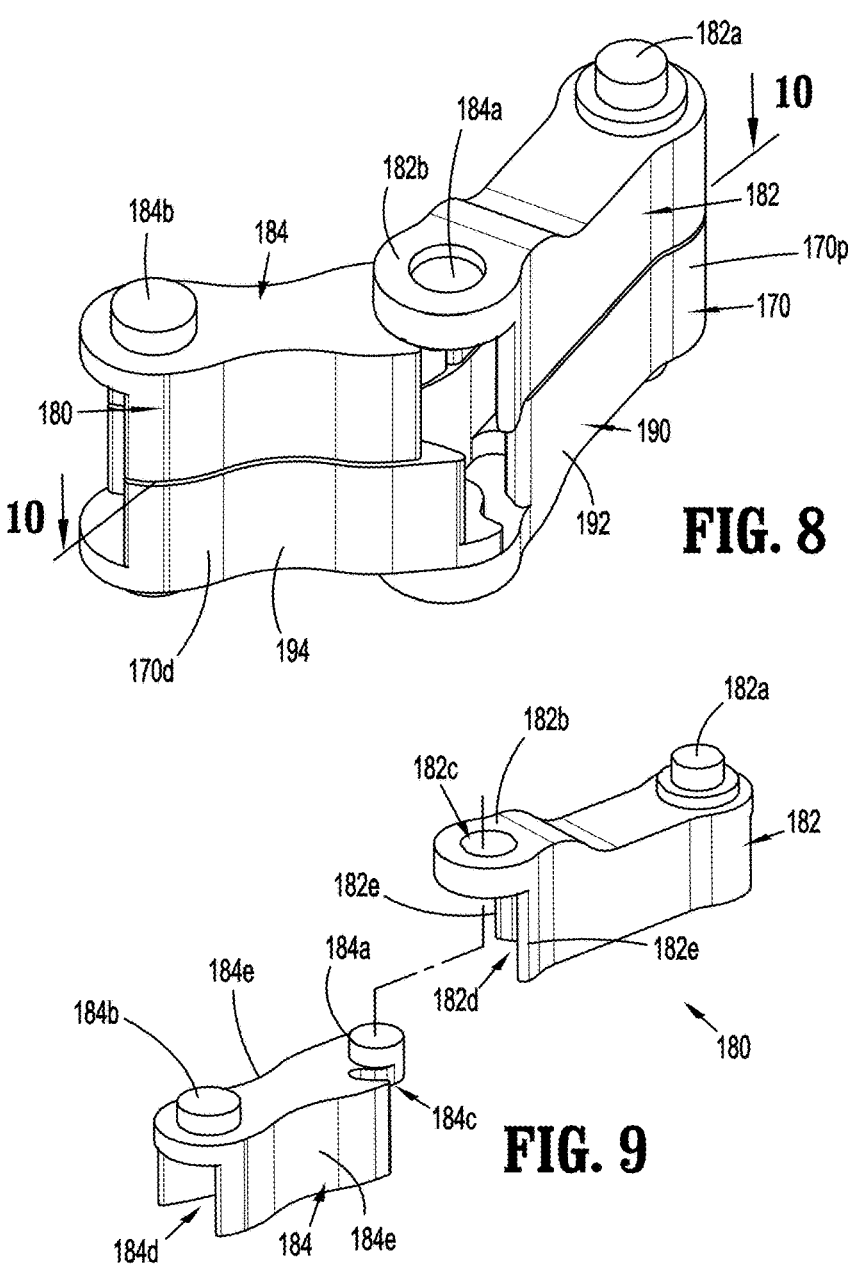
FIG. 8
FIG. 9
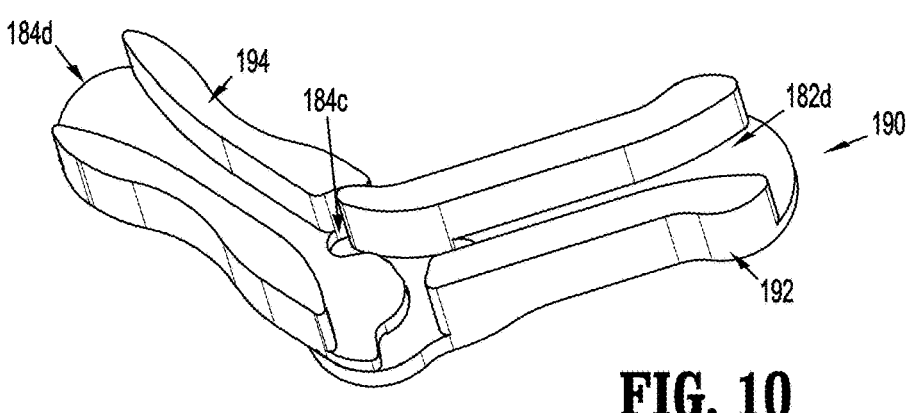
FIG. 10

ARTICULATING SURGICAL STAPLING APPARATUS WITH PIVOTABLE KNIFE BAR GUIDE ASSEMBLY

CROSS REFERENCE TO RELATED APPLICATIONS

This application is a continuation of U.S. patent application Ser. No. 17/665,962, filed on Feb. 7, 2022, which is a continuation-in-part of U.S. patent application Ser. No. 17/407,628, filed on Aug. 20, 2021, now U.S. Pat. No. 11,707,277, the entire contents of each of which are incorporated by reference herein.

TECHNICAL FIELD

This disclosure relates to surgical stapling apparatus, devices and/or systems for performing surgical procedures and methods of use thereof.

BACKGROUND

Surgical stapling apparatus that clamp, cut and/or staple tissue are well known in the art. Such surgical stapling apparatus include end effectors having two elongated jaw members used to capture or clamp tissue. One of the two jaw members usually carries a staple cartridge that houses a plurality of staples positioned in rows, while the other of the two jaw members has an anvil for forming the staples as the staples are driven from the staple cartridge. For instance, in linear surgical stapling apparatus, a stapling operation is effectuated by a cam bar, a drive sled or other similar mechanism having a cam member that travels longitudinally through channels defined in the staple cartridge and acts upon staple pushers in the channels to sequentially eject linear rows of staples from the staple cartridge. A knife, often supported on a drive beam, is movably positioned between the linear rows of staples such that when the surgical stapling apparatus is positioned about tissue and actuated, the tissue is joined and/or simultaneously or nearly simultaneously cut.

Some surgical stapling apparatus include reloads (sometimes referred to as loading units) and handle assemblies. The reloads may include articulatable end effectors with various articulation angles relative to the handle assemblies. With linear stapling, greater articulation is always desirable with a shorter dead space (e.g., distance from an articulation joint to where a staple line starts). To facilitate articulation, surgical stapling apparatus can include rotatable bar guides to guide knife bars. As the bar guides rotate when the jaw members are articulated, the bar guides can cause the knife bars to distally advance where the greater the articulation, the greater the distal advancement. Advancing of the drive beam requires increased dead space to provide for extra movement and/or require the articulation and drive beam travel to be timed together (e.g., simultaneous two motor movement).

SUMMARY

This disclosure details surgical stapling apparatus including a bar guide assembly that prevents bar buckling and maintains length during articulation such that a drive beam of the surgical stapling apparatus does not travel upon articulation. Advantageously, the bar guide assembly may be doubled hinged to enable increased articulation and mechanical articulation independent of drive beam travel.

Further, the surgical stapling apparatus may include an articulation link with a guide ramp that reduces bend tightness and dead space. In particular, the guide ramp may enable the bar guide assembly to rotate outwardly before bending inwardly to provide a gradual bend. The associated bend path enables the drive beam to be positioned farther back than in stapling apparatus with standard bend paths, thereby providing shorter dead space. This bending movement maintains the drive beam length constant during articulation whereby the drive beam does not move forward during articulation. This bending movement enables articulation and linear drive to be independent of one another, for example, at least up to approximately 50 degrees of articulation relative to a central longitudinal axis of the surgical stapling apparatus. This disclosure also reduces the need for homing the surgical stapling apparatus after a loading unit is secured to the surgical stapling apparatus.

In accordance with one aspect, this disclosure is directed to a surgical stapling apparatus that includes a shaft assembly, an end effector secured to the shaft assembly, a firing assembly, and an articulation assembly. The firing assembly includes a drive beam and a flexible knife bar assembly that are selectively advanceable through the end effector for firing the end effector. The articulation assembly has an articulation link assembly and a pivotable bar guide assembly. The articulation link assembly is coupled to the end effector and actuatable to cause the end effector to articulate relative to the shaft assembly. The pivotable bar guide assembly supports the flexible knife bar assembly and includes a proximal guide assembly and a distal guide assembly that are pivotably coupled together. The proximal guide assembly is pivotably coupled to the shaft assembly. The distal guide assembly is pivotably coupled to the end effector.

In aspects, the pivotable bar guide may pivot in response to an actuation of articulation link assembly. The articulation link assembly may include a proximal articulation link and a distal articulation link that are pivotably coupled together. The distal articulation link may have a proximal end portion coupled to a distal end portion of the proximal articulation link, and a distal end portion coupled to a proximal end portion of the end effector. The proximal articulation link may include a guide ramp positioned to engage the pivotable bar guide when the end effector articulates relative to the shaft assembly.

In aspects, the proximal guide assembly may include a proximal boss that pivotably couples to the shaft assembly. The proximal guide assembly may include a distal hoop defining a boss opening therethrough. The distal guide assembly may include a proximal boss that is received within the boss opening of the distal hoop of the proximal guide assembly to pivotably couple the proximal and distal guide assemblies together. The distal guide assembly may include a distal boss that pivotably couples to a proximal end portion of the end effector. The proximal end portion of the end effector may include a mounting assembly. The mounting assembly may define a boss bore therein that receives the distal boss of the distal guide assembly to pivotably couple the distal guide assembly to the mounting assembly.

In aspects, the pivotable bar guide assembly may define a central passage therethrough that slidably receives the knife bar assembly.

According to another aspect, this disclosure is directed to a surgical stapling apparatus including a housing assembly, an adapter assembly extending from the housing assembly, and a reload selectively attachable to the adapter assembly. The reload supports an end effector on a distal end portion of the reload. The reload includes a firing assembly and an articulation assembly. The firing assembly includes a drive beam and a flexible knife bar assembly that are selectively advanceable through the end effector for firing the end effector. The articulation assembly has an articulation link assembly and a pivotable bar guide assembly. The articulation link assembly is coupled to the end effector and actuatable to cause the end effector to articulate relative to the shaft assembly. The pivotable bar guide assembly supports the flexible knife bar assembly and includes a proximal guide assembly and a distal guide assembly that are pivotably coupled together. The proximal guide assembly is pivotably coupled to the shaft assembly. The distal guide assembly is pivotably coupled to the end effector.

In accordance with yet another aspect, this disclosure is directed to a reload for a surgical stapling apparatus. The reload includes a shaft assembly, an end effector, an articulation link assembly, and a pivotably bar guide assembly. The end effector supports a drive beam and a flexible knife bar assembly that are selectively advanceable through the end effector for firing the end effector. The articulation link assembly is coupled to the end effector and actuatable to cause the end effector to articulate relative to the shaft assembly. The pivotable bar guide assembly is configured to bend the flexible knife bar assembly when the end effector articulates relative to the shaft assembly. The pivotable bar guide assembly includes a proximal guide assembly and a distal guide assembly that are pivotably coupled together. The proximal guide assembly is pivotably coupled to the shaft assembly. The distal guide assembly is pivotably coupled to the end effector.

In accordance with one aspect, this disclosure is directed to a surgical stapling apparatus that includes a shaft assembly, an end effector secured to the shaft assembly, a firing assembly, an articulation assembly, and an articulation guide. The firing assembly includes a flexible knife bar assembly that is selectively advanceable through the end effector for firing the end effector. The articulation assembly has an articulation link assembly and a pivotable bar guide assembly. The articulation link assembly is coupled to the end effector. The articulation link assembly is actuatable to cause the end effector to move relative to the shaft assembly between an unarticulated position and an articulated position. The articulation guide is associated with the pivotable bar guide assembly to enable the flexible knife bar assembly to advance through the pivotable bar guide assembly when the end effector is disposed in the unarticulated position or the articulated position.

In aspects, the pivotable bar guide may pivot in response to an actuation of the articulation link assembly. The articulation link assembly may include a proximal articulation link and a distal articulation link that are pivotably coupled together.

In some aspects, the articulation guide may include a kicker cam, and wherein the kicker cam may extend from the distal articulation link and may engage the pivotable bar guide assembly. The pivotable bar guide assembly may include a proximal guide assembly and a distal guide assembly that are pivotably coupled together. The kicker cam may be configured to slide along an outer surface of the distal guide assembly. The outer surface of the distal guide assembly may include a side bulge, a recess, or combinations thereof that the kicker cam contacts to facilitate articulating movement of the distal guide assembly.

In aspects, the pivotable bar guide assembly may include a proximal guide assembly and a distal guide assembly that are pivotably coupled together. The proximal guide assembly may be pivotably coupled to the shaft assembly. The distal guide assembly may be pivotably coupled to the end effector.

In aspects, the articulation guide may include a detent mechanism associated with the distal guide assembly that facilitates articulating movement of the distal guide assembly.

In aspects, the articulation guide may include a leaf spring that is coupled to the proximal guide assembly to urge the proximal guide assembly to a centered position when articulated.

According to another aspect of this disclosure, a surgical stapling apparatus includes a housing assembly, an adapter assembly extending from the housing assembly, and a reload selectively attachable to the adapter assembly. The reload supports an end effector on a distal end portion of the reload. The reload includes a firing assembly, an articulation assembly, and an articulation guide. The firing assembly includes a flexible knife bar assembly that is selectively advanceable through the end effector for firing the end effector. The articulation assembly has an articulation link assembly and a pivotable bar guide assembly. The articulation link assembly is coupled to the end effector. The articulation link assembly is actuatable to cause the end effector to move relative to the adapter assembly between an unarticulated position and an articulated position. The articulation guide is associated with the pivotable bar guide assembly to enable the flexible knife bar assembly to advance through the pivotable bar guide assembly when the end effector is disposed in the unarticulated position or the articulated position.

In accordance with still another aspect of this disclosure, a reload for a surgical stapling apparatus includes a shaft assembly, an end effector, an articulation link assembly, a pivotable bar guide assembly, and an articulation guide. The end effector supports a flexible knife bar assembly that is selectively advanceable through the end effector for firing the end effector. The articulation link assembly is coupled to the end effector and actuatable to cause the end effector to articulate relative to the shaft assembly between an unarticulated position and an articulated position. The pivotable bar guide assembly is configured to bend the flexible knife bar assembly when the end effector articulates relative to the shaft assembly. The articulation guide is associated with the pivotable bar guide assembly to enable the flexible knife bar assembly to advance through the pivotable bar guide assembly when the end effector is disposed in the unarticulated position or the articulated position.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate aspects of the disclosure and, together with a general description of the disclosure given above, and the detailed description of the aspect(s) given below, explain the principles of the disclosure, wherein:

FIG. 8 is a perspective view of a bar guide assembly of the surgical stapling apparatus of FIG. 1;

FIG. 9 is a perspective view, with parts separated, of an upper guide assembly of the bar guide assembly of FIG. 8;

FIG. 10 is a perspective view of a lower guide assembly of the bar guide assembly of FIG. 8;

DETAILED DESCRIPTION

Figure 1:
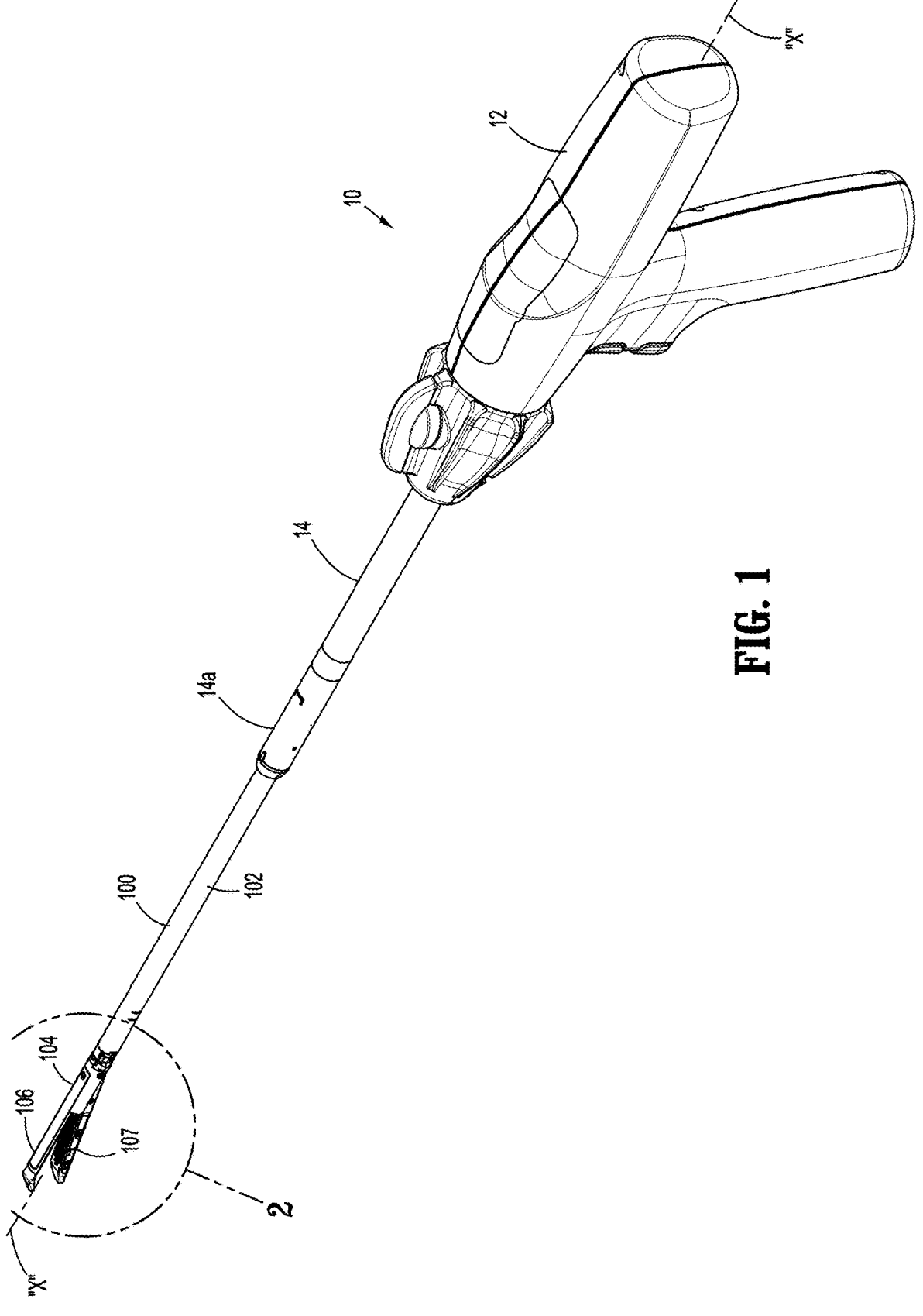
FIG. 1 is a perspective view of a surgical stapling apparatus in accordance with the principles of this disclosure.

Aspects of the disclosed surgical stapling apparatus are described in detail with reference to the drawings, in which like reference numerals designate identical or corresponding elements in each of the several views. As commonly known, the term "clinician" refers to a doctor, a nurse, or any other care provider and may include support personnel. Additionally, the term "proximal" refers to the portion of structure that is closer to the clinician and the term "distal" refers to the portion of structure that is farther from the clinician. In addition, directional terms such as front, rear, upper, lower, top, bottom, and the like are used simply for convenience of description and are not intended to limit the disclosure attached hereto. As used herein, the term "endoscopic" is used generally used to refer to endoscopic, laparoscopic, arthroscopic, and/or any other procedure conducted through a small diameter incision or cannula.

As used herein, the terms parallel and perpendicular are understood to include relative configurations that are substantially parallel and substantially perpendicular up to about + or −10 degrees from true parallel and true perpendicular.

In the following description, well-known functions or constructions are not described in detail to avoid obscuring the present disclosure in unnecessary detail.

Further, although the surgical stapling apparatus are generally shown and described herein in connection with a linear surgical stapling system for brevity, the disclosed surgical stapling apparatus can include any powered, manual, or robotically-controlled surgical stapling systems such as a circular stapler, a transverse stapler, or an open stapler. For a detailed description of the structure and function of exemplary surgical stapling systems, one or more components of which may be included, or modified for use with the disclosed aspects, reference may be made to U.S. Pat. Nos. 9,713,470; 8,806,973; 8,256,656; 8,157,152; 8,070,033; 7,819,896; 7,770,774; 7,334,717; 7,128,253; 5,964,394; and 5,915,616, the entire contents of each of which are incorporated herein by reference.

With reference to FIGS. 1-12, a surgical stapling apparatus 10 of this disclosure includes a housing assembly 12 (which may include one or more handles that may be manually actuatable to fire surgical stapling apparatus 10), an adapter assembly 14 secured to housing assembly 12 and extending distally from housing assembly 12, and a reload 100 secured to adapter assembly 14 and extending distally from adapter assembly 14. Adapter assembly 14 and reload 100 define a longitudinal axis "X-X" that extends longitudinally therealong. Reload 100 may be reusable, disposable and/or include one or more reusable and/or disposable components. Housing assembly 12 may be in the form of a powered housing assembly that provides powered actuation of reload 100 via adapter assembly 14.

Reload 100 of surgical stapling apparatus 10 is releasably secured to a distal end portion 14*a* of adapter assembly 14 and includes a shaft assembly 102 that supports an end effector 104 on a distal end portion of shaft assembly 102. End effector 104 includes an anvil assembly 106 and a cartridge assembly 107 that houses a plurality of fasteners or staples in a plurality of rows of staple slots 108*a* defined in a staple cartridge 108 of cartridge assembly 104. The plurality of rows of staple slots 108*a* are supported on opposed sides of a knife slot 108*c* defined through staple cartridge 108. Staple cartridge 108 is selectively attachable to a support plate 109 that is pivotably coupled to anvil assembly 106 via pivot pins 111. Staple cartridge 108 may be selectively removable from support plate 109 and replaceable. Anvil assembly 106 includes an anvil 110 defining a plurality of rows of staple pockets 110*a* (FIG. 6) therein that correspond with the plurality of rows of staple slots 108*a* of staple cartridge 108 so that the plurality of staples can be dispensed from staple slots 108*a* of staple cartridge 108 and formed against staple pockets 110*a* of anvil 110 upon a firing of surgical stapling apparatus 10.

Figures 2, 3:
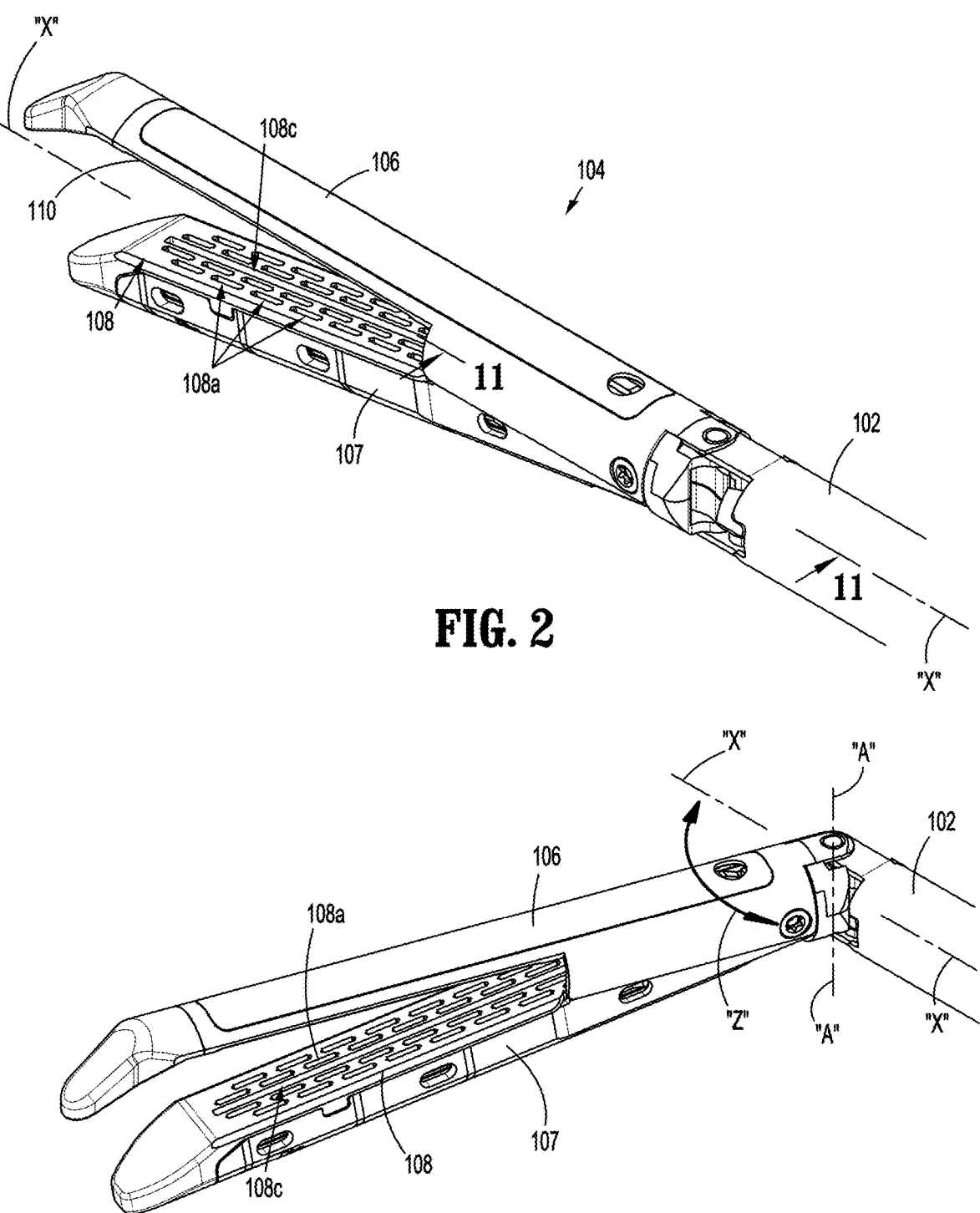
FIG. 2 is an enlarged, perspective view of the indicated area of detail illustrating an end effector of the surgical stapling apparatus of FIG. 1 in an unarticulated position.
FIG. 3 is another perspective view illustrating the end effector of FIG. 2 in an articulated position.
Figures 4, 5:
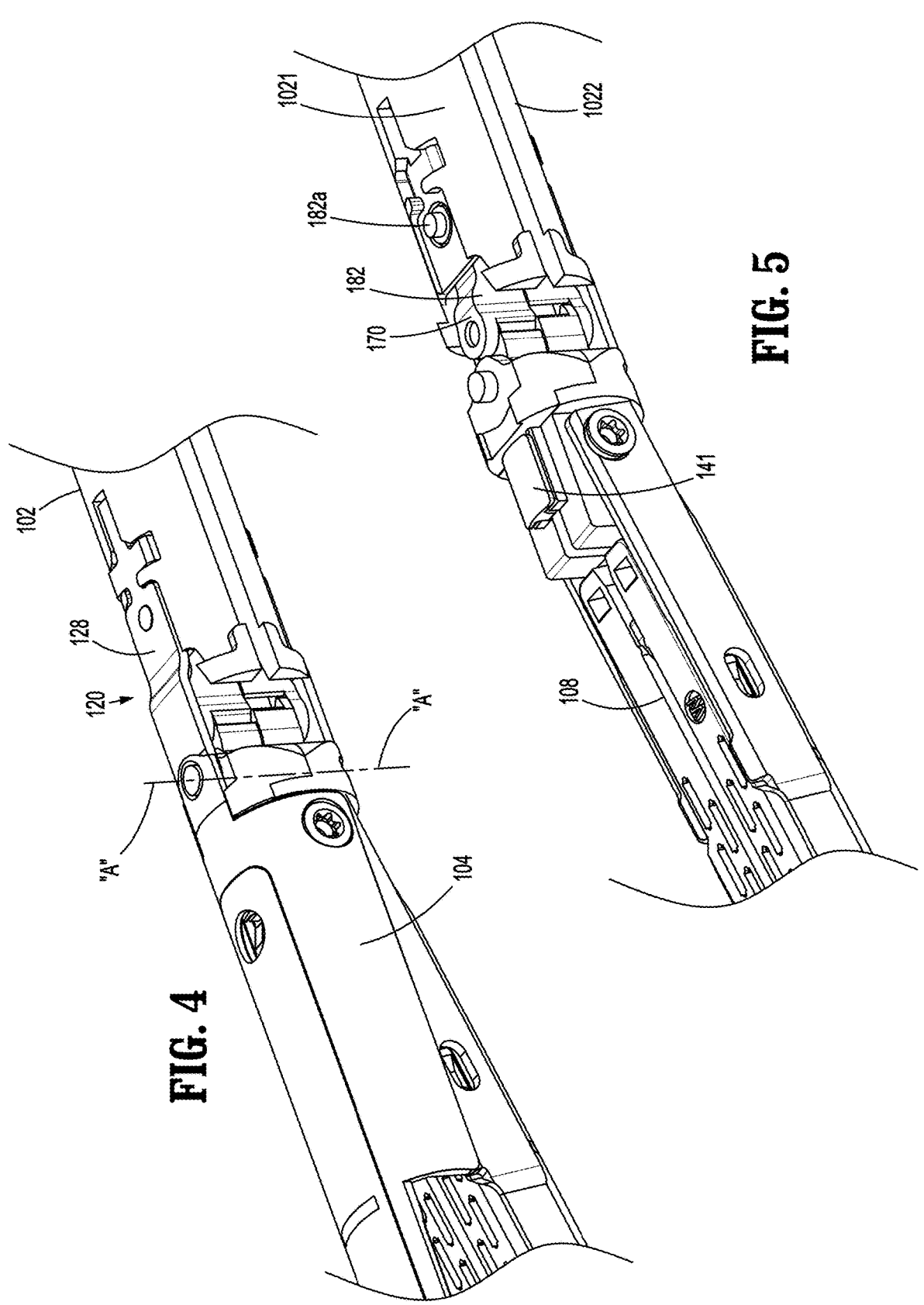
FIGS. 4-6 are enlarged, perspective views of distal portions of the surgical stapling apparatus of FIG. 1, the distal portions shown with portions thereof removed for clarity.
Figure 6:
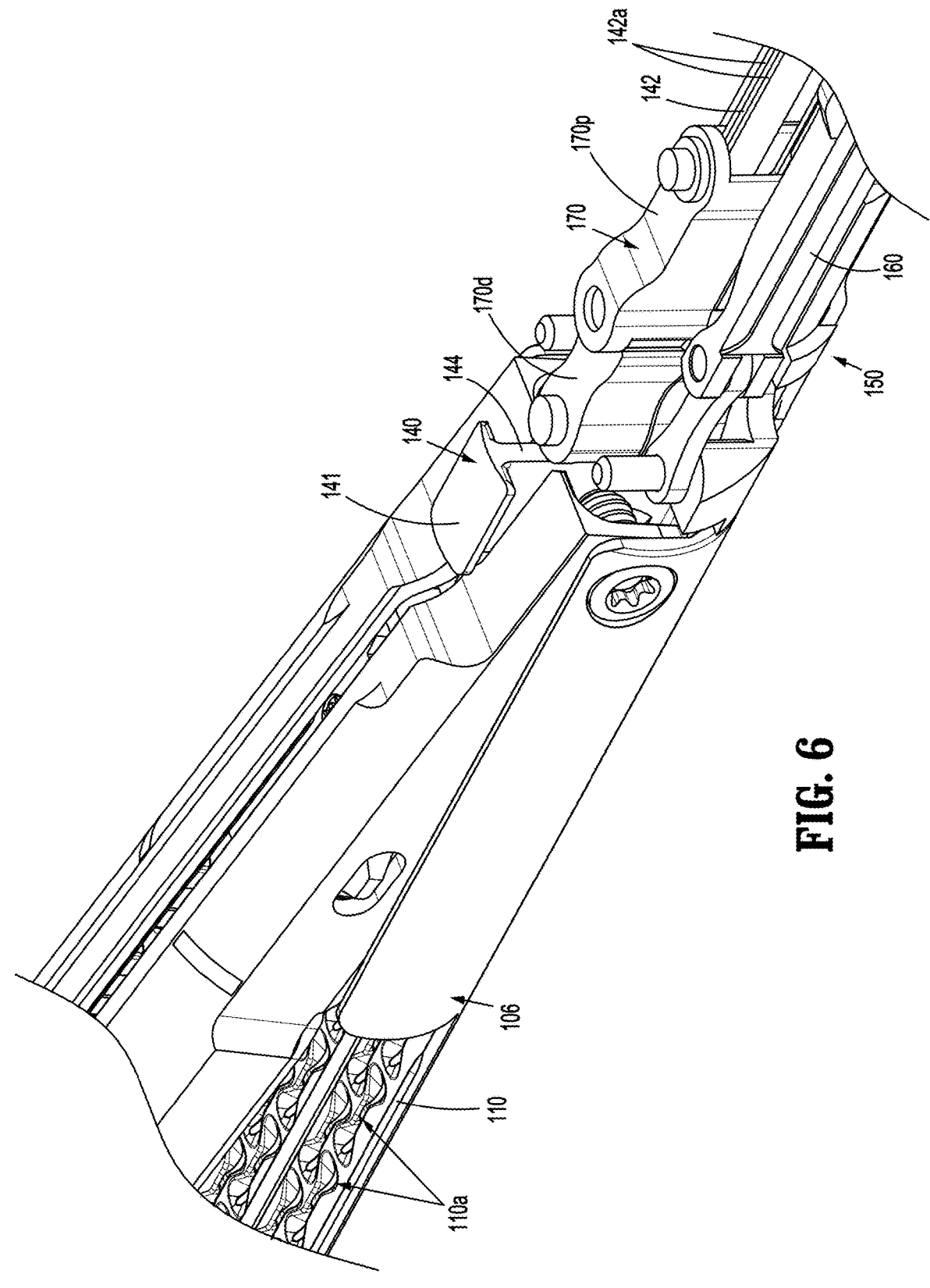
Figure 7:
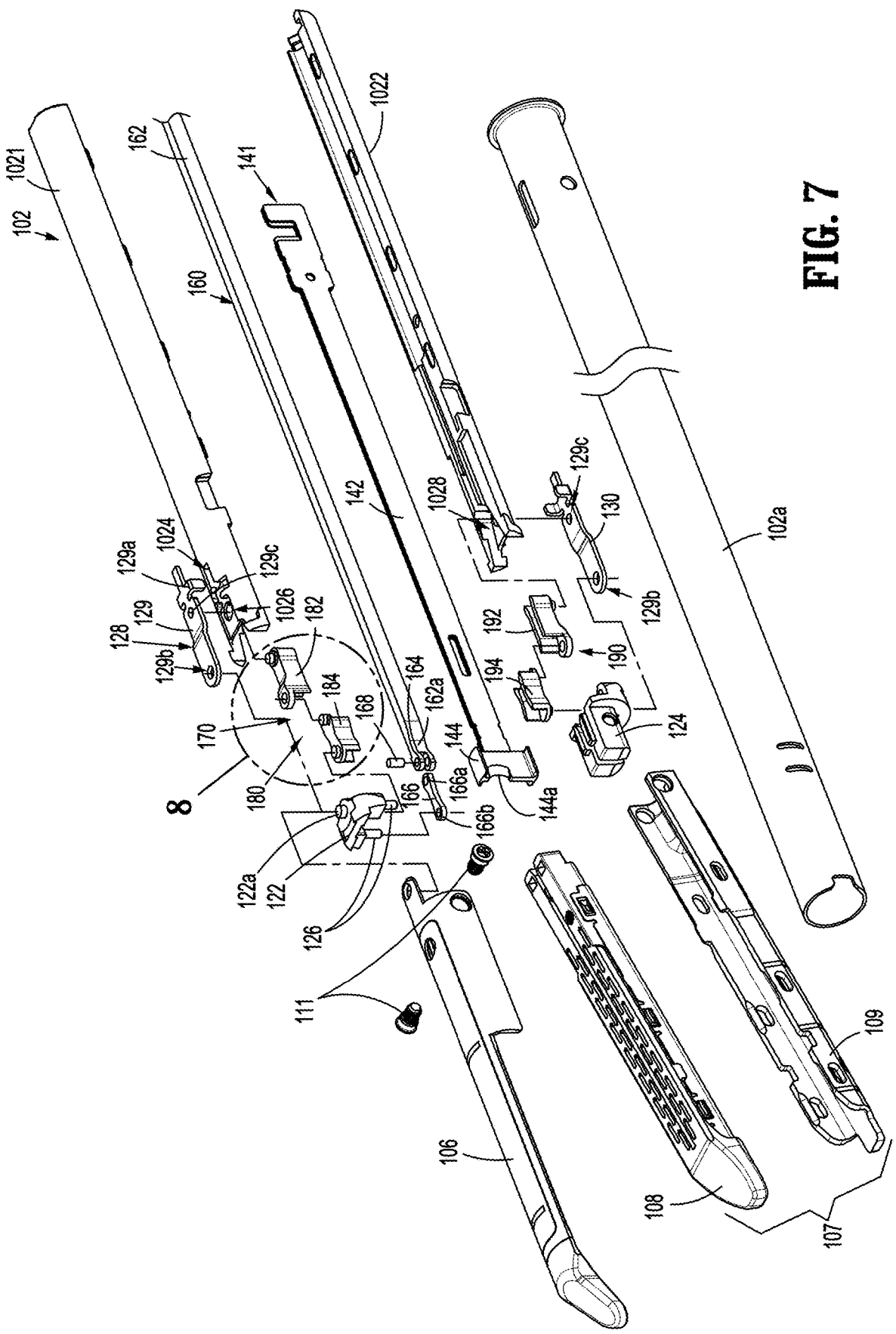
FIG. 7 is a perspective view, with parts separated, of a distal portion of the surgical stapling apparatus of FIG. 1.
Figure 11:
FIG. 11 is an enlarged, cross-sectional view as taken along section line 11-11 of FIG. 2.
Figure 12:
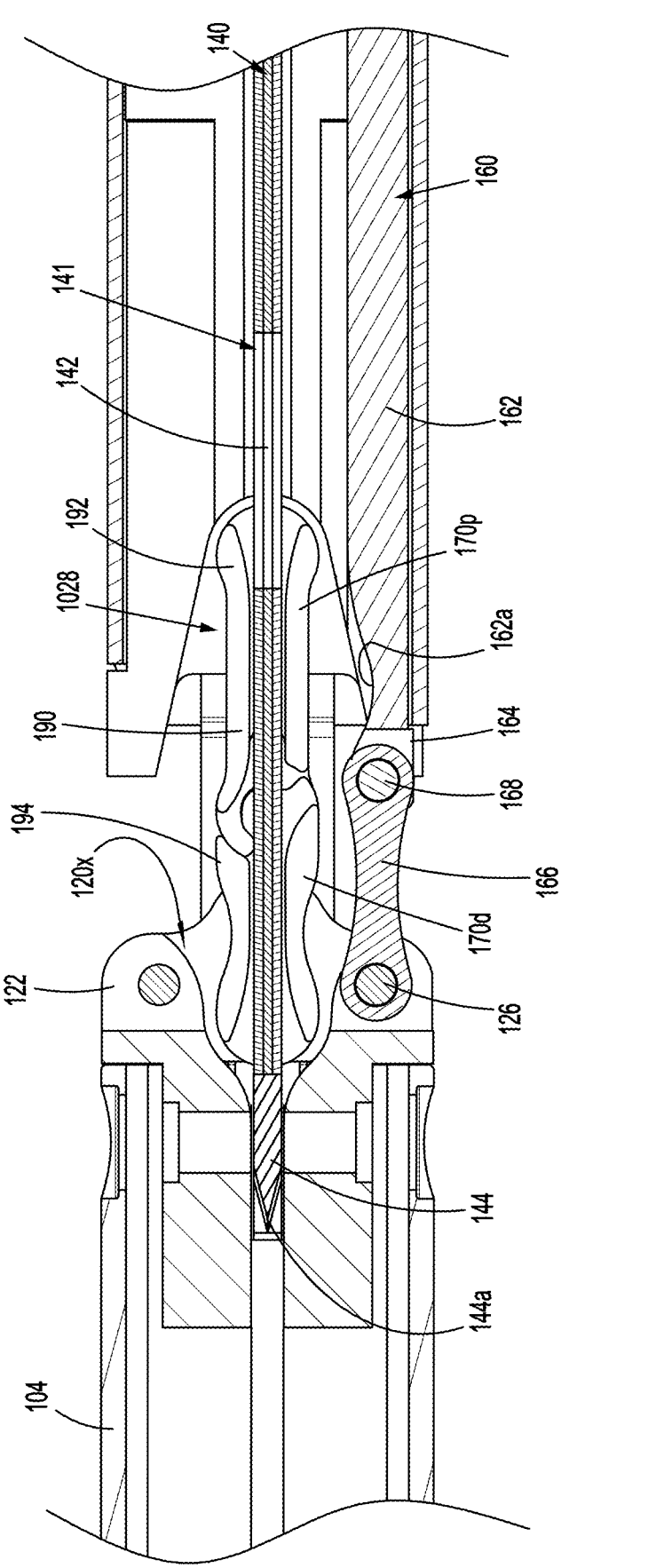
FIG. 12 is a cross-sectional view as taken along section line 12-12 of FIG. 11 with the surgical stapling apparatus shown in the unarticulated position.
Figure 13:
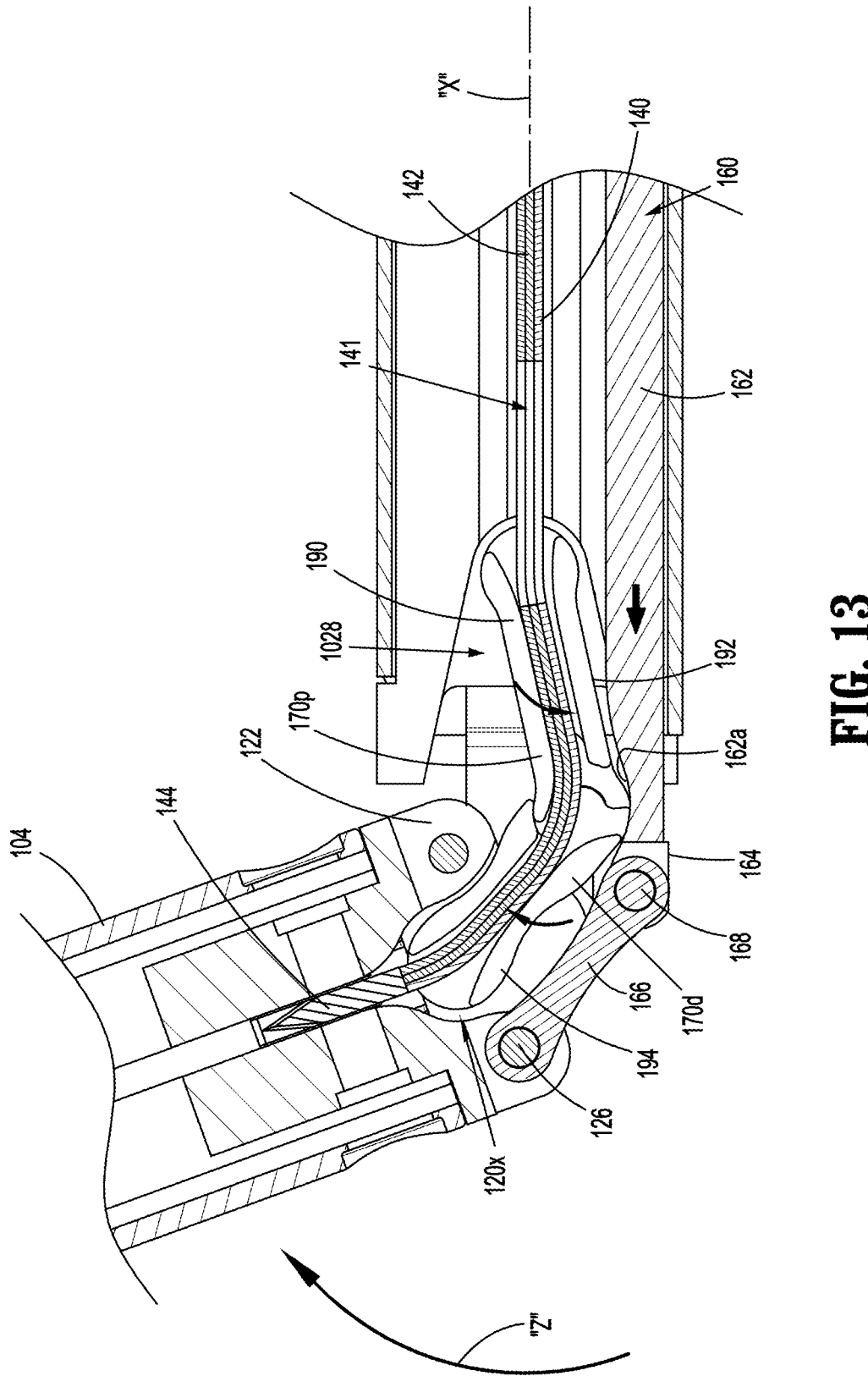
FIG. 13 is a view of FIG. 12 illustrating the surgical stapling apparatus in a first articulated position.
Figure 14:
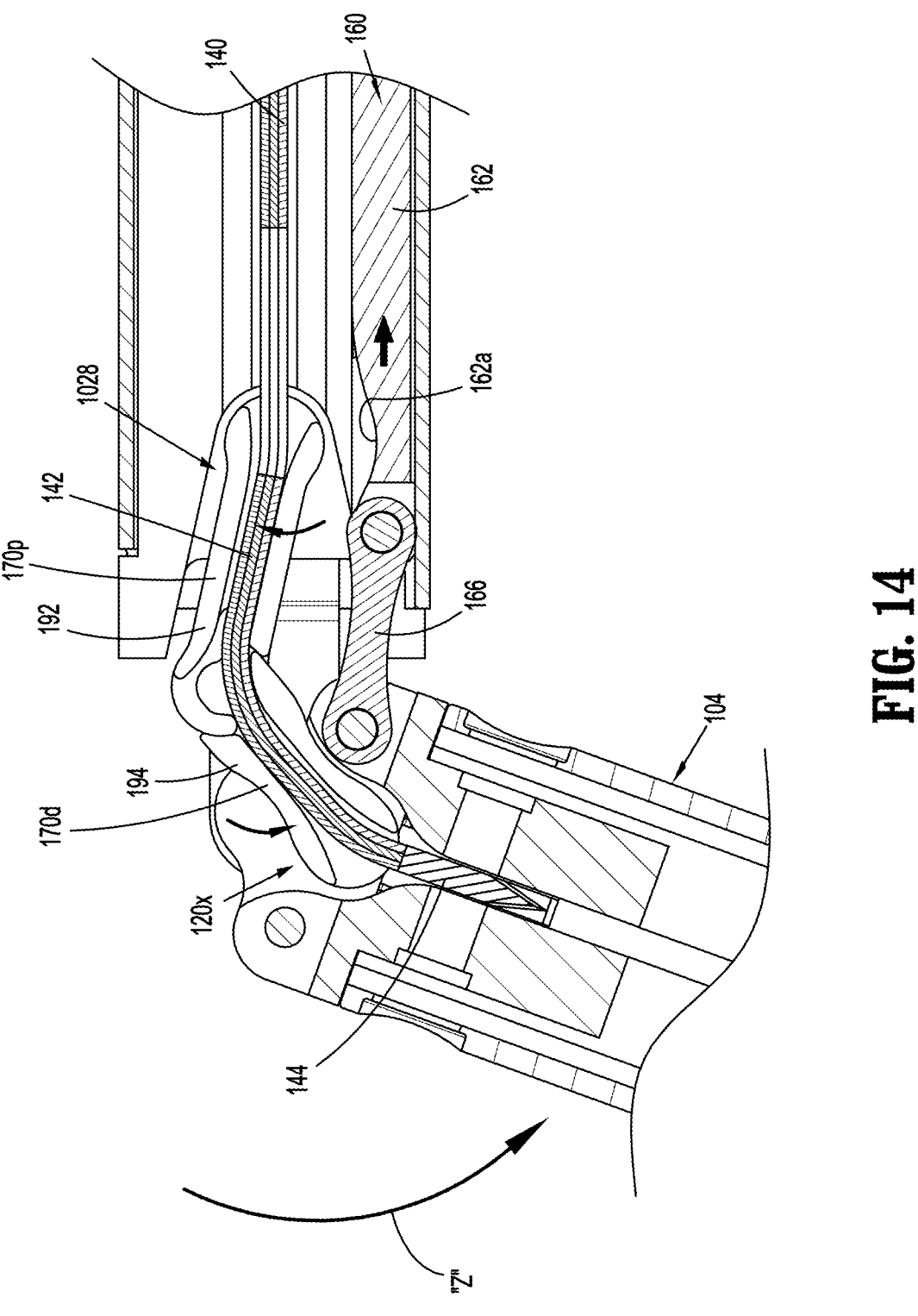
FIG. 14 is a view of FIG. 12 illustrating the surgical stapling apparatus in a second articulated position.
Figures 15, 16:
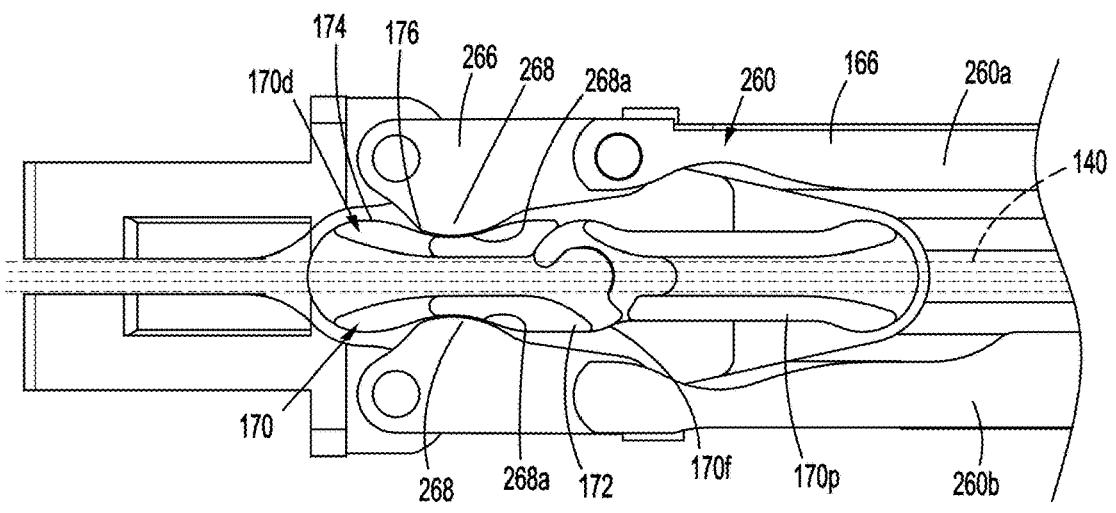
FIG. 15 is a perspective view of another distal portion of the surgical stapling apparatus of FIG. 1 in accordance with another aspect, the distal portion shown with portions thereof removed for clarity.
FIGS. 16-20 are top progressive views of a portion of the distal portion of FIG. 15, the views illustrating movement of the distal portion between unarticulated and articulated positions.

Reload 100 of surgical stapling apparatus 10 supports shaft assembly 102 on a proximal end portion thereof and end effector 104 on a distal end portion thereof. End effector 104 is pivotably coupled to shaft assembly 102 by a mounting assembly 120 that enables end effector 104 to articulate relative to shaft assembly 102 about an articulation axis "A-A" extending through mounting assembly 120, as indicated by arrows "Z." In particular, end effector 104 may pivot about articulation axis "A-A" from an unarticulated position (FIG. 2), aligned with longitudinal axis "X-X" of surgical stapling apparatus 10, to an articulated position (FIG. 3). Mounting assembly 120 includes an upper mounting block 122 and a lower mounting block 124 that are pinned together via mount pins 126 extending from upper mounting block 122. Upper mounting block 122 includes an upper coupler pin 122*a* extending therefrom and lower mounting block 124 includes a lower coupler pin 124*a* depending therefrom (see FIG. 11). Upper coupler pin 122*a* pivotably supports an upper coupling arm 128 and lower coupler pin 124*a* pivotably supports a lower coupling arm 130. Upper and lower coupling arms 128, 130 extend from mounting assembly 120 and secure mounting assembly 120 to shaft assembly 102. Mounting assembly 120 further defines a proximally-facing concave recess 120*x* therein (FIG. 12).

Each of upper and lower coupling arms 128, 130 includes an elongated body 129 having a hooked proximal end portion 129*a* and a distal coupler pin opening 129*b* defined therethrough. Elongated body 129 further defines a proximal pin opening 129*c* therethrough.

Shaft assembly 102 of reload 100 includes an outer sleeve 102*a* and an inner shaft assembly 102*b* supported within outer sleeve 102*a*. Inner shaft assembly 102*b* includes an upper shaft housing 1021 and a lower shaft housing 1022 that couple together and define coupler cutouts 1024 in outer surfaces of distal end portions thereof. Upper and lower shaft housings 1021, 1022 have identical structure and are disposed in mirrored relation to one another. Coupler cutouts 1024 of upper and lower shaft housings 1021, 1022 are configured to receive hooked proximal end portions 129*a* of respective upper and lower coupling arms 128, 130 therein for fixedly securing upper and lower coupling arms 128, 130 to upper and lower shafts housings 1021, 1022. The distal end portions of upper and lower shafts housings 1021, 1022 further define pin apertures 1026 therethrough that are disposed in registration with proximal pin openings 129*c* of respective upper and lower coupling arms 128, 130. The distal end portion of upper and lower shaft housings 1021, 1022 further define a distally facing concave recess 1028 therein.

Reload 100 of surgical stapling apparatus 10 further includes a firing assembly 140 having a drive beam assembly 141 and sled 143 that is disposed in cartridge assembly 107 for dispensing staples therefrom. Drive beam assembly 141 has a proximal end portion that is operatively coupled to adapter assembly 14 of surgical stapling apparatus 10. Drive beam assembly 141 has a knife bar assembly 142 and a drive beam 144 secured to a distal end portion of knife bar assembly 142 for engagement with sled 143. Knife bar assembly 142 is flexible and includes a plurality of laminates 142*a* coupled together. Drive beam 144 may be in the form of an I-beam and includes a knife 144*a*.

Reload 100 further includes an articulation assembly 150 having an articulation link assembly 160 and a pivotable bar guide assembly 170 that is double hinged.

Articulation link assembly 160 of articulation assembly 150 includes a proximal articulation link 162 having a clevis 164 supported on a distal end portion thereof and a guide ramp 162*a* defined in the distal end portion of articulation link 162 adjacent to a proximal end portion of clevis 164. Articulation link assembly 160 further includes a distal articulation link 166 having a proximal snare 166*a* and a distal snare 166*b*. Proximal snare 166*a* is received by clevis 164 and pinned thereto via link pin 168. Distal snare 166*b* is coupled to a mount pin 126 of upper mounting block 122.

Pivotable bar guide assembly 170 of articulation assembly 150 includes an upper guide assembly 180 and a lower guide assembly 190 that are coupled together.

Upper guide assembly 180 includes a proximal upper guide 182 and a distal upper guide 184, and lower guide assembly 190 includes a proximal lower guide 192 and a distal lower guide 194. Upper guide assembly 180 and lower guide assembly 190 having mirrored structure such that proximal upper guide 182 and proximal lower guide 192 are identical (but inverted versions of one another) and together form a proximal guide assembly 170*p*. Distal upper guide 184 and distal lower guide 194 are identical (but inverted versions of one another) and together form a distal guide assembly 170*d*. Given the symmetry of structure between the upper and lower guide assemblies 180, 190, only upper guide assembly 180 is described hereinbelow for brevity.

As best seen in FIGS. 8-11, proximal upper guide 182 of upper guide assembly 180 includes a proximal boss 182*a* projecting from an upper surface thereof and a distal hoop 182*b* extending distally from proximal upper guide 182. Distal hoop 182*b* defines a boss opening 182*c* therethrough. Proximal upper guide 182 further defines a central passage 182*d* therethrough. Proximal upper guide 182 further includes distal abutments 182*e* depending from distal hoop 182*b*.

Distal upper guide 184 of upper guide assembly 180 includes a proximal boss 184*a* that is received within boss opening 182*c* of proximal upper guide 182 to pivotably couple distal upper guide 184 and proximal upper guide 182 together. Distal upper guide 184 further includes a distal boss 184*b* that is received within a boss bore 122*b* defined within a lower surface of upper mounting block 122 to pivotably couple distal upper guide 184 to upper mounting block 122—notably, a distal boss 184*b* of distal lower guide 194 of lower guide assembly 190 pivotably couples to a boss bore 124*b* defined within an upper surface of lower mounting block 124 as seen in FIG. 11. Distal upper guide 184 of upper guide assembly 180 further defines a side slot 184*c* defined in a proximal portion of distal upper guide 184 adjacent to proximal boss 184*a*. Distal upper guide 184 also defines a central passage 184*d* therethrough. Distal upper guide 184 further includes concave sidewalls 184*e* along a central portion thereof. Central passages 182*d*, 184*d* of upper guide assembly 180 are configured to slidably receive knife bar assembly 142 of drive beam assembly 141 therethrough.

In use, as best seen in FIGS. 2, 3, and 12-14, articulation link assembly 160 can be actuated to distally advance proximal articulation link 162. Distal advancement of proximal articulation link 162 causes distal articulation link 166 to distally advance and pivot about link pin 168 and mount pin 126 to which distal articulation link 166 is coupled. The distal and pivoting movement of distal articulation link 166 articulates end effector 104 in a first direction (e.g., laterally to the right) relative to the longitudinal axis "X" and shaft assembly 102. As end effector 104 articulates in the first direction, proximal guide assembly 170*p* pivots about proximal bosses 182*a* in a second direction opposite to the first direction (e.g., laterally to the left) and relative to the longitudinal axis "X." The proximal guide assembly 170*p* can pivot in the second direction until a distal end portion (e.g., distal hoops 182*b*) of proximal guide assembly 170*p* engages guide ramp 162*a* of proximal articulation link 162. Guide ramp 162*a* enables pivotable guide bar assembly 170 to cam therealong and facilitate pivotal movement of pivotable guide bar assembly 170. Such pivoting movement causes a proximal end portion of distal guide assembly 170*d* of pivotable guide bar assembly 170 to pivot with the distal end portion of proximal guide assembly 170*p* of pivotable guide bar assembly 170 while a distal end portion of distal guide assembly 170*d* pivots in the first direction with end effector 104. This movement causes pivotable bar guide assembly 170 to bend the portion of knife bar assembly 142 disposed within pivotable bar guide assembly 170 so that upon an actuation of firing assembly 140, knife bar assembly 142 can be distally advanced through end effector 104 when end effector 104 is disposed in such an articulated position to fire surgical stapling apparatus 10.

Articulation link assembly 160 can be actuated to proximally move proximal articulation link 162 so that end effector 104 can be articulated in the second direction. In particular, proximal movement of proximal link 162 of articulation link assembly 160 draws distal articulation link 166 proximally and pivots end effector 104 such that proximal guide assembly 170p pivots in the first direction and distal guide assembly 170d pivots in the second direction to thereby bend the portion of knife bar assembly 142 disposed within pivotable bar guide assembly 170. Again, upon an actuation of firing assembly 140, knife bar assembly 142 can be distally advanced through end effector 104 when end effector 104 is disposed in such an articulated position to fire surgical stapling apparatus 10. Of course, firing assembly 140 can be actuated to advance knife bar assembly 142 distally through the end effector 104 when end effector 104 is in an unarticulated position to fire surgical stapling apparatus 10.

Turning now to FIGS. 15-20, in aspects, articulation assembly 150 includes articulation link assemblies 260 that cooperate with pivotable bar guide assembly 170. Each articulation link assembly 260 includes a proximal articulation link 162 and a distal articulation link 266 that is similar to distal articulation link 166 but includes an articulation guide in the form of a kicker cam 268. Kicker cam 268 has a rounded edge 268a that is disposed in contacting relationship with an outer surface 170f of distal guide assembly 170d of pivotable bar guide assembly 170 to urge distal guide assembly 170 toward a predetermined direction of articulation of end effector 104 as rounded edges 268a of articulation link assemblies 260 cam along outer surface 170f of distal guide assembly 170d.

Outer surface 170f of distal guide assembly 170d includes a proximal side bulge 172, a distal side bulge 174, and a recessed intermediate portion 176 that is disposed between the proximal and distal side bulges 172, 174.

Figures 17, 18:
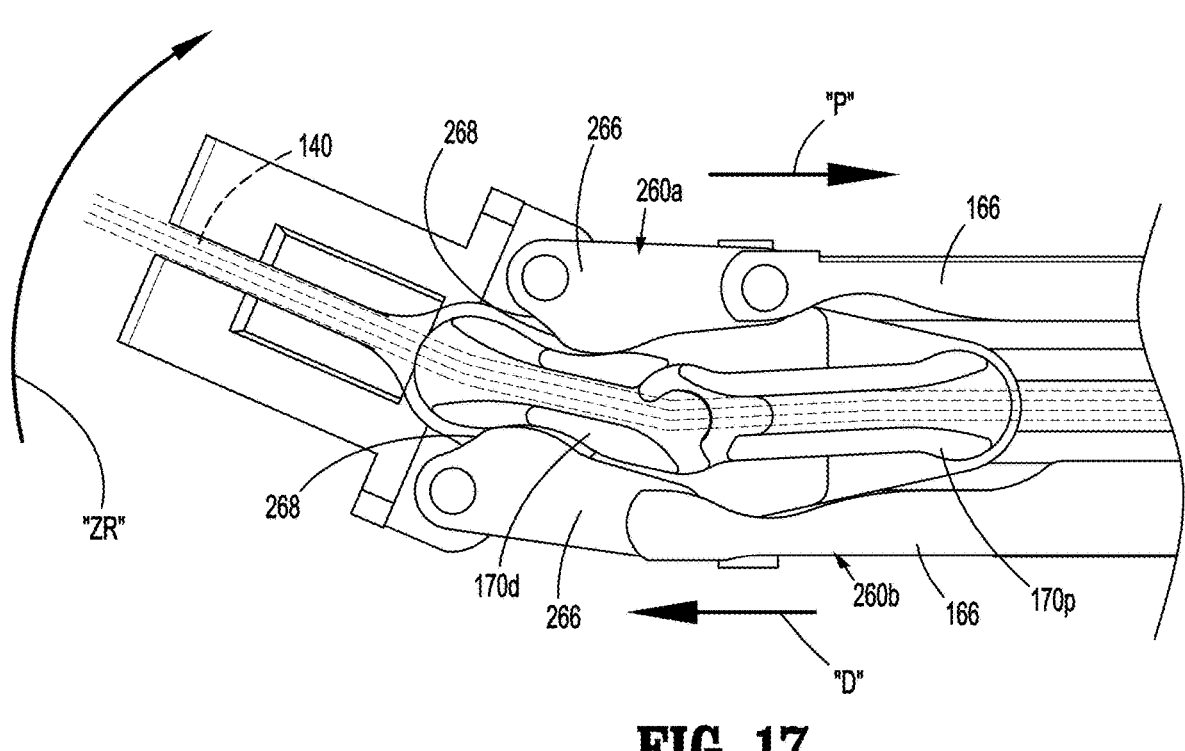

As seen in FIGS. 17 and 18, when a first articulation link assembly 260a of articulation link assemblies 260 is moved in a proximal direction, as indicated by arrow "P," a second articulation link assembly 260b of articulation link assemblies 260 is moved in a distal direction, as indicated by arrow "D," such that articulation link assemblies 260a, 260b urge articulation of end effector 104 in a first direction (e.g., to the right), as indicated by arrow "ZR." In such instance, kicker cam 268 of first articulation link assembly 260a cams proximally out of recessed intermediate portion 176 and proximally along proximal side bulge 172 as kicker cam 268 of second articulation link assembly 260b cams distally out of recessed intermediate portion 176 and distally along distal side bulge 174 causing distal guide assembly 170d to pivot in a clockwise direction, as indicated by arrow "C," as proximal guide assembly 170p pivots in a counterclockwise direction, as indicated by arrow "CC."

Figure 19:
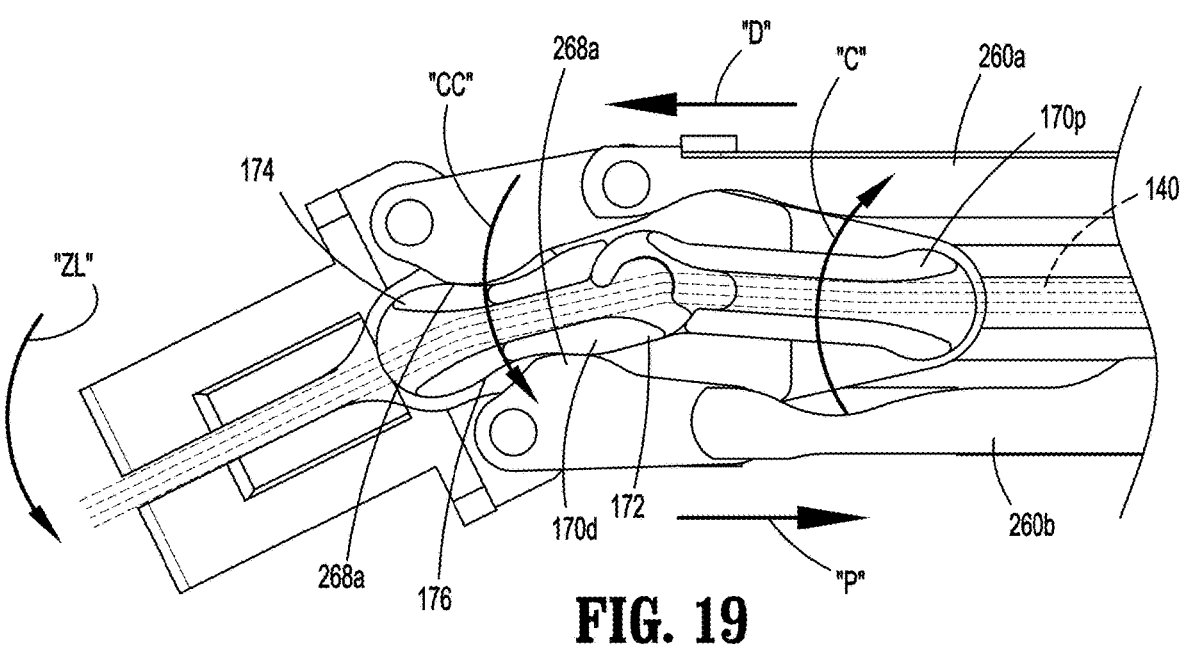
Figure 20:
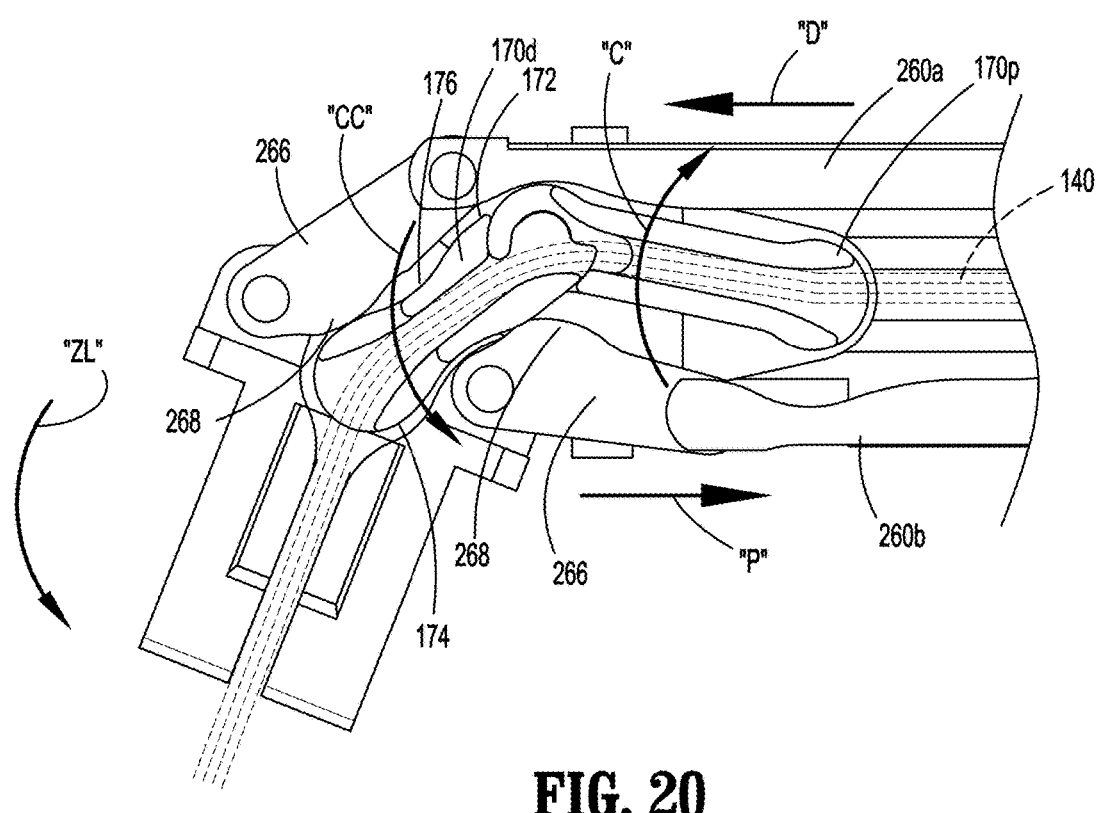

Conversely, as illustrated in FIGS. 19 and 20, when first articulation link assembly 260a is moved in a distal direction, second articulation link assembly 260b moves in a proximal direction such that articulation link assemblies 260a, 260b urge articulation of end effector 104 in a second direction (e.g., to the left) opposite to the first direction, as indicated by arrow "ZL." In such instance, kicker cam 268 of second articulation link assembly 260b cams proximally out of recessed intermediate portion 176 and proximally along proximal side bulge 172 as kicker cam 268 of first articulation link assembly 260a cams distally out of recessed intermediate portion 176 and distally along distal side bulge 174 causing distal guide assembly 170d to pivot in a counterclockwise direction, as indicated by arrow "CC," as proximal guide assembly 170p pivots in a clockwise direction, as indicated by arrow "C."

Notably, the respective distal articulation link 266 of the first or second articulation link assembly 260a, 260b moving in the proximal direction pivots in the same general clockwise or counterclockwise direction as the proximal guide assembly 170p. However, rotation rates of the respective distal articulation link 266 and the proximal guide assembly 170p may be the same and/or different, and may depend on the articulation angle; radii of kicker cams 268, side bulges 172, 174, and/or recessed intermediate portion 176; and/or distances between axes of rotation between articulation link assemblies 260a, 260b and pivotable bar guide assembly 170, or portions thereof. Meanwhile, the respective distal articulation link 266 of the other of the first or second articulation link assemblies 260a, 260b moving in the distal direction pivots in the same general clockwise or counterclockwise direction as the distal guide assembly 170d. However, rotation rates of the respective distal articulation link 266 and the distal guide assembly 170d may be the same and/or different, and may also depend on the articulation angle; radii of kicker cams 268, side bulges 172, 174, and/or recessed intermediate portion 176; and/or distances between axes of rotation between articulation link assemblies 260a, 260b and pivotable bar guide assembly 170, or portions thereof.

Figures 21, 22:
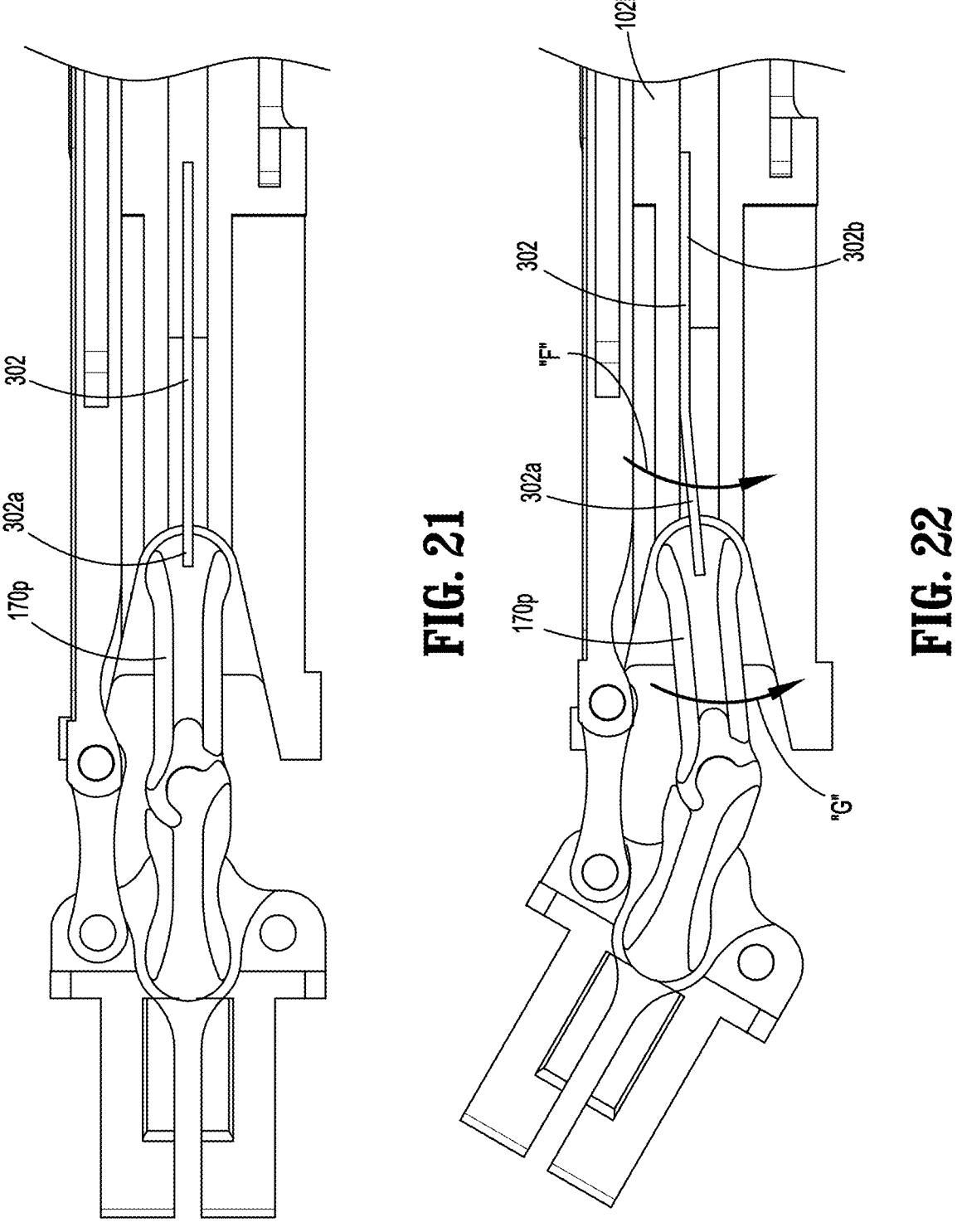
FIGS. 21 and 22 are top progressive views of still another distal portion of the surgical stapling apparatus of FIG. 1 in accordance with still another aspect, the views illustrating movement of the distal portion between unarticulated and articulated positions.
Figures 23, 24:
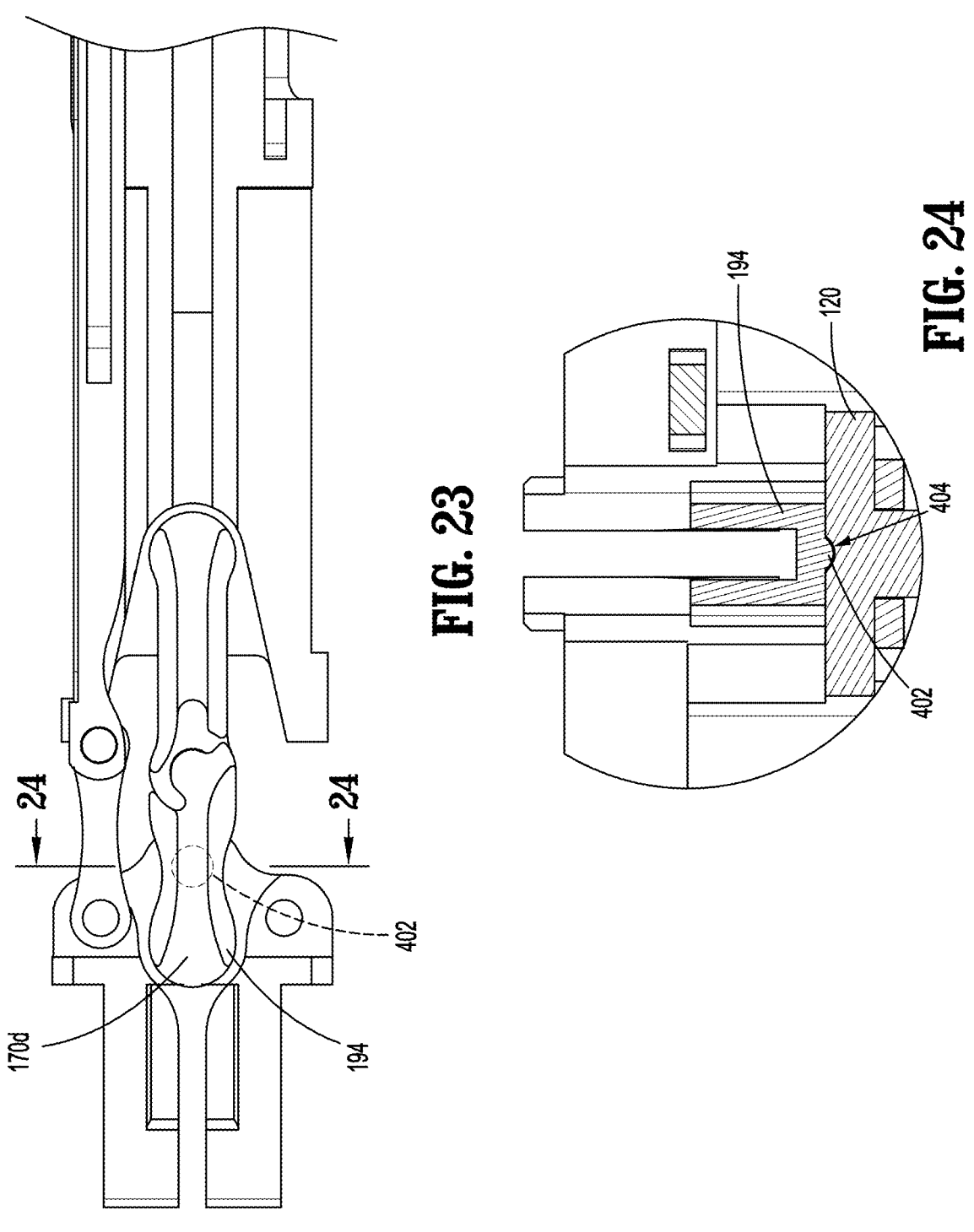
FIG. 23 is a top view of yet another distal portion of the surgical stapling apparatus of FIG. 1 in accordance with yet another aspect.
FIG. 24 is a cross-sectional view of FIG. 23 as taken along section line 24-24.
Figures 25, 26:
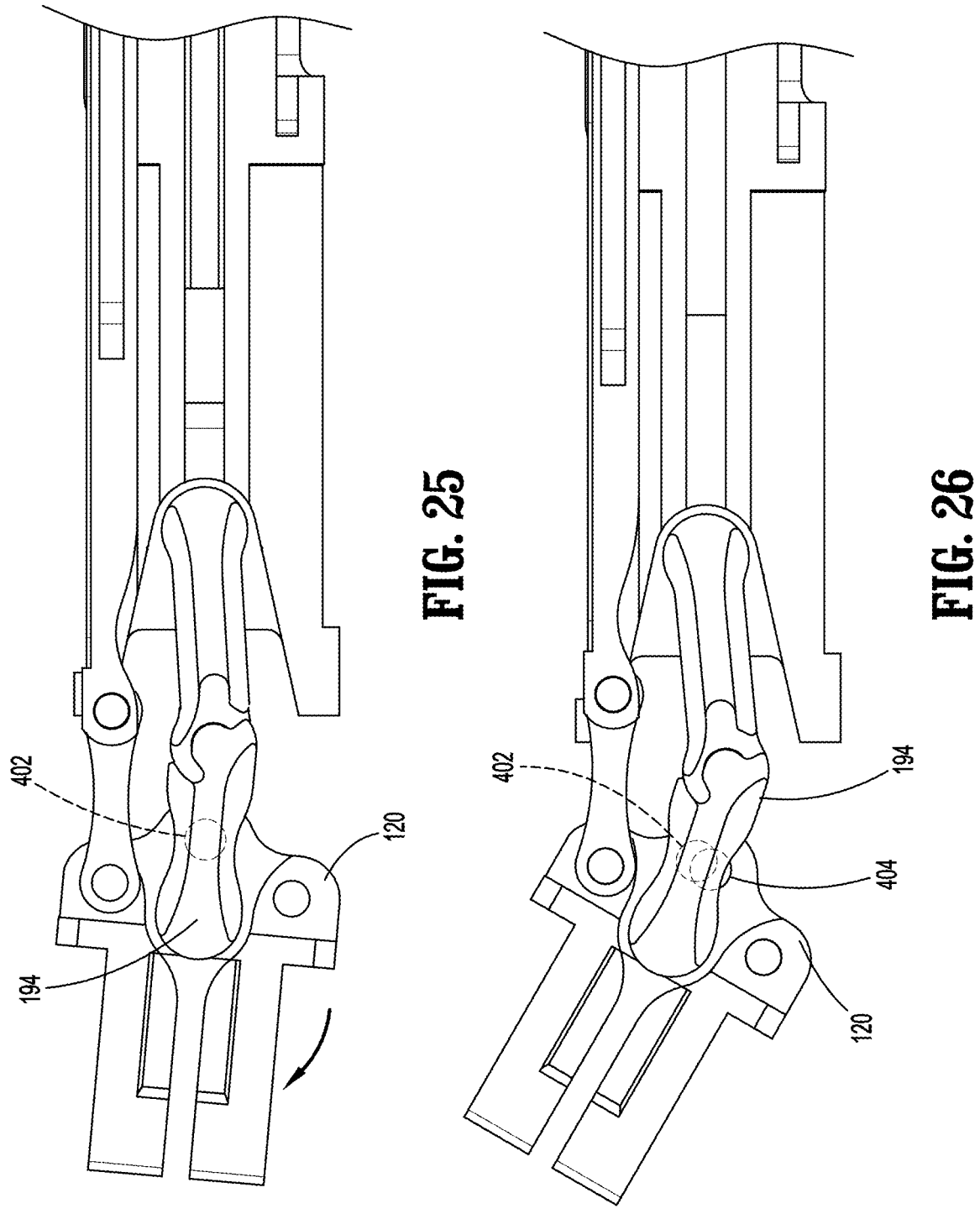
FIGS. 25 and 26 are top progressive views of the distal portion of FIG. 23, the views illustrating movement of the distal portion between unarticulated and articulated positions.

With reference to FIGS. 21 and 22, in one aspect, proximal guide assembly 170p includes an articulation guide in the form of a leaf spring 302 having a distal end portion 302a coupled to a proximal end portion of proximal guide assembly 170p. Leaf spring 302 includes a proximal end portion 302b that is coupled to inner shaft assembly 102b. Distal end portion 302a of leaf spring 302 is configured to flex or articulate, as indicated by arrow "F," relative to proximal end portion 302b of leaf spring 302 as proximal guide assembly 170p pivots or articulates, as indicated by arrow "G." Leaf spring 302 is configured to urge proximal guide assembly 170p toward an initial or unarticulated/unflexed position (FIG. 21) when distal end portion 302a of leaf spring 302 is flexed relative to proximal end portion 302b of leaf spring 302. In aspects, leaf spring 302 may be centered in the unflexed position thereof.

Referring to FIGS. 23-26, in another aspect, articulation guide can be in the form of a detent mechanism including a detent 402 and a detent bore 404. In particular, distal guide assembly 170d, for example, distal lower guide 194 of distal guide assembly 170d, can include detent 402, which may extend from a bottom surface of distal lower guide 194. Mounting assembly 120 may define detent bore 404 therein. Detent bore 404 is configured to selectively receive detent 402 therein. Detent 402 and detent bore 404 are configured to urge distal guide assembly 170d to properly articulate. In aspects, distal guide assembly 170d may define detent bore 404 and mounting assembly 120 may include detent 402 extending therefrom.

Notably, the bend radius and firing strength requirements of knife bars are highly particular, especially when articulating 25 degrees or more. With such requirements, knife bar set (yielding) can occur (e.g., permanent bends in the laminates 142a of knife bar assembly 142) in response to articulation of end effector 104. Advantageously, the aspects illustrated in FIGS. 15-26 help to prevent pivotable bar guide assembly 170 from inadvertently binding when articulating the knife bar assembly 142 in different directions, particularly when knife bar set occurs. Specifically, these aspects help to center pivotable bar guide assembly 170 and overcome knife bar set so that pivotable bar guide assembly 170 can flex/articulate without binding as the end effector 104 is articulated in either or both directions.

Securement of any of the components of the presently disclosed apparatus may be effectuated using known securement techniques such welding, crimping, gluing, fastening, etc.

The various aspects disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical workstations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary aspects, and that the description, disclosure, and figures should be construed merely as exemplary of aspects. It is to be understood, therefore, that the present disclosure is not limited to the precise aspects described, and that various other changes and modifications may be effected by one skilled in the art without departing from the scope or spirit of the disclosure. Additionally, the elements and features shown or described in connection with certain aspects may be combined with the elements and features of certain other aspects without departing from the scope of the present disclosure, and that such modifications and variations are also included within the scope of the present disclosure. Accordingly, the subject matter of the present disclosure is not limited by what has been particularly shown and described.

What is claimed is:

1. A surgical stapling apparatus, comprising:
   a shaft assembly extending longitudinally in proximal and distal directions;
   an end effector secured to a distal end portion of the shaft assembly;

a firing assembly including a flexible knife bar assembly that is selectively advanceable through the end effector for firing the end effector;
an articulation assembly including:
   a pivotable bar guide assembly having a proximal guide assembly and a distal guide assembly pivotably coupled together about a common axis and positioned to receive the flexible knife bar assembly, with the proximal guide assembly pivotably coupled to the shaft assembly, and the distal guide assembly pivotably coupled to the end effector; and
   an articulation link assembly coupled to the end effector, the articulation link assembly being actuatable to cause the end effector to move relative to the shaft assembly between an unarticulated position and an articulated position; and
an articulation guide comprising at least one of a kicker cam or a detent mechanism and disposed in contacting relationship with the pivotable bar guide assembly to urge the pivotable bar guide assembly toward a predetermined direction of articulation.

2. The surgical stapling apparatus of claim 1, wherein the pivotable bar guide assembly articulates in response to an actuation of the articulation link assembly.

3. The surgical stapling apparatus of claim 2, wherein the articulation link assembly includes a proximal articulation link and a distal articulation link.

4. The surgical stapling apparatus of claim 1, wherein the articulation guide includes the kicker cam, and wherein the kicker cam is configured to slide along an outer surface of the distal guide assembly.

5. The surgical stapling apparatus of claim 4, wherein the outer surface of the distal guide assembly includes a side bulge, a recess, or combinations thereof that the kicker cam contacts to facilitate articulating movement of the distal guide assembly.

6. The surgical stapling apparatus of claim 1, wherein the kicker cam has a rounded edge that extends in a direction toward the firing assembly.

7. The surgical stapling apparatus of claim 6, wherein the rounded edge of the kicker cam is configured to cam axially along the pivotable bar guide assembly.

8. The surgical stapling apparatus of claim 1, wherein the articulation guide comprises the detent mechanism with a detent disposed on the distal guide assembly.

9. The surgical stapling apparatus of claim 8, further comprising a mounting assembly securing the end effector to the shaft assembly, with the detent mechanism further including a detent bore disposed on the mounting assembly and receiving the detent when the end effector is in the unarticulated position.

10. A surgical stapling apparatus, comprising:
    a housing assembly;
    an adapter assembly extending from the housing assembly; and
    a reload selectively attachable to the adapter assembly, the reload extending longitudinally between proximal and distal directions and supporting an end effector on a distal end portion of the reload, the reload including:
       a firing assembly including a flexible knife bar assembly that is selectively advanceable through the end effector for firing the end effector;
       a pivotable bar guide assembly having a proximal guide assembly pivotably coupled to a distal guide assembly and positioned to receive the flexible knife bar assembly; and an articulation link assembly coupled to the end effector, the articulation link assembly being actuatable to cause the end effector to move between an unarticulated position and an articulated position, the articulation link assembly including an articulation guide comprising a kicker cam that is movable relative to the pivotable bar guide assembly to urge the pivotable bar guide assembly toward a predetermined direction of articulation;

wherein axial movement of the kicker cam in a first direction causes the pivotable bar guide assembly to articulate in a clockwise direction, and wherein axial movement of the kicker cam in a second direction causes the pivotable bar guide assembly to articulate in a counterclockwise direction; and wherein when the kicker cam moves distally, the distal guide assembly is configured to articulate in the same direction as the kicker cam.

11. The surgical stapling apparatus of claim 10, wherein when the kicker cam moves proximally to a predetermined location, the kicker cam is configured to articulate in the same direction as the distal guide assembly.

12. The surgical stapling apparatus of claim 11, wherein when the kicker cam moves proximally past the predetermined location, the kicker cam and the distal guide assembly are configured to articulate in different directions.

13. The surgical stapling apparatus of claim 12, wherein when the kicker cam moves distally, the proximal guide assembly and the kicker cam are configured to articulate in different directions.

14. The surgical stapling apparatus of claim 13, wherein when the kicker cam moves proximally to the predetermined location, the kicker cam and the proximal guide assembly are configured to articulate in different directions.

15. The surgical stapling apparatus of claim 14, wherein when the kicker cam moves proximally past the predetermined location, the kicker cam and the proximal guide assembly are configured to articulate in the same direction.

16. A reload for a surgical stapling apparatus, the reload comprising:

a shaft assembly extending longitudinally in proximal and distal directions;

an end effector supporting a flexible knife bar assembly that is selectively advanceable through the end effector for firing the end effector;

a pivotable bar guide assembly, comprising:

a distal guide assembly having a vertically projecting boss; and a proximal guide assembly having a hoop with a boss opening receiving the boss; and an articulation link assembly coupled to the end effector and actuatable to cause the end effector to articulate between an unarticulated position and an articulated position, the articulation link assembly including an articulation guide that is movable relative to the pivotable bar guide assembly to articulate the pivotable bar guide assembly relative to or with the articulation guide.

* * * * *